United States Patent
Peters et al.

(10) Patent No.: US 9,445,602 B2
(45) Date of Patent: Sep. 20, 2016

(54) ELECTROLYTIC SYSTEM AND METHOD FOR GENERATING BIOCIDES HAVING AN ELECTRON DEFICIENT CARRIER FLUID AND CHLORINE DIOXIDE

(71) Applicant: STRATEGIC RESOURCE OPTIMIZATION, INC., Bailey, CO (US)

(72) Inventors: Michael J. Peters, Bailey, CO (US); John D. Breedlove, Boulder, CO (US); Seth R. Meyer, Broomfield, CO (US)

(73) Assignee: Strategic Resource Optimization, Inc., Bailey, CO (US)

( * ) Notice: Subject to any disclaimer, the term of this patent is extended or adjusted under 35 U.S.C. 154(b) by 35 days.

(21) Appl. No.: 13/797,787

(22) Filed: Mar. 12, 2013

(65) Prior Publication Data

US 2016/0044926 A1    Feb. 18, 2016

Related U.S. Application Data

(63) Continuation-in-part of application No. 12/947,818, filed on Nov. 16, 2010, now Pat. No. 8,394,253.

(51) Int. Cl.

| | |
|---|---|
| *C02F 1/461* | (2006.01) |
| *C25B 15/02* | (2006.01) |
| *A01N 59/00* | (2006.01) |
| *C25B 9/08* | (2006.01) |
| *C25B 1/26* | (2006.01) |
| *C25B 15/08* | (2006.01) |
| *C02F 1/467* | (2006.01) |
| *C02F 1/42* | (2006.01) |

(52) U.S. Cl.
CPC ............. *A01N 59/00* (2013.01); *C02F 1/4674* (2013.01); *C25B 1/26* (2013.01); *C25B 9/08* (2013.01); *C25B 15/02* (2013.01); *C25B 15/08* (2013.01); *C02F 1/42* (2013.01); *C02F 2201/4617* (2013.01); *C02F 2201/4618* (2013.01); *C02F 2201/4619* (2013.01); *C02F 2201/46115* (2013.01); *C02F 2201/46165* (2013.01); *C02F 2209/006* (2013.01); *C02F 2209/04* (2013.01); *C02F 2209/05* (2013.01); *C02F 2209/06* (2013.01)

(58) Field of Classification Search
None
See application file for complete search history.

(56) References Cited

U.S. PATENT DOCUMENTS

| | | | | |
|---|---|---|---|---|
| 4,247,531 | A  * | 1/1981 | Hicks | C01B 11/024 210/754 |
| 4,329,215 | A  * | 5/1982 | Scoville | C02F 1/4674 204/228.2 |
| 4,530,743 | A  * | 7/1985 | deNora | C25B 1/46 204/263 |
| 5,965,009 | A  * | 10/1999 | Shimamune | C02F 1/4618 204/263 |
| 2009/0181107 | A1 * | 7/2009 | Buckley | C02F 1/46104 424/661 |
| 2012/0121731 | A1 * | 5/2012 | Peters | C02F 1/4674 424/722 |

* cited by examiner

*Primary Examiner* — Harry D Wilkins, III
(74) *Attorney, Agent, or Firm* — Polsinelli PC

(57) ABSTRACT

A method for electrolytically generating a biocide, including providing a brine solution carrier fluid; providing a vessel for creating a first passageway and a second passageway, flowing the carrier fluid through the vessel; applying an electric potential to the electrodes to produce an anolyte fluid, an anolyte gas, a catholyte fluid, and a catholyte gas in the vessel; removing the anolyte fluid, anolyte gas, catholyte fluid, and catholyte gas from the vessel; mixing a portion of the anolyte gas with the catholyte fluid to produce ozone gas and hypochlorite bleach mixture; re-circulating the ozone gas with the ozone gas and hypochlorite bleach mixture; mixing the anolyte fluid with the hypochlorite bleach solution; mixing a chlorite brine with the hypochlorite bleach solution to produce a chlorite brine/hypochlorite bleach solution mixture; and mixing the anolyte fluid with the chlorite brine/hypochlorite bleach solution mixture to the produce the biocide.

13 Claims, 11 Drawing Sheets

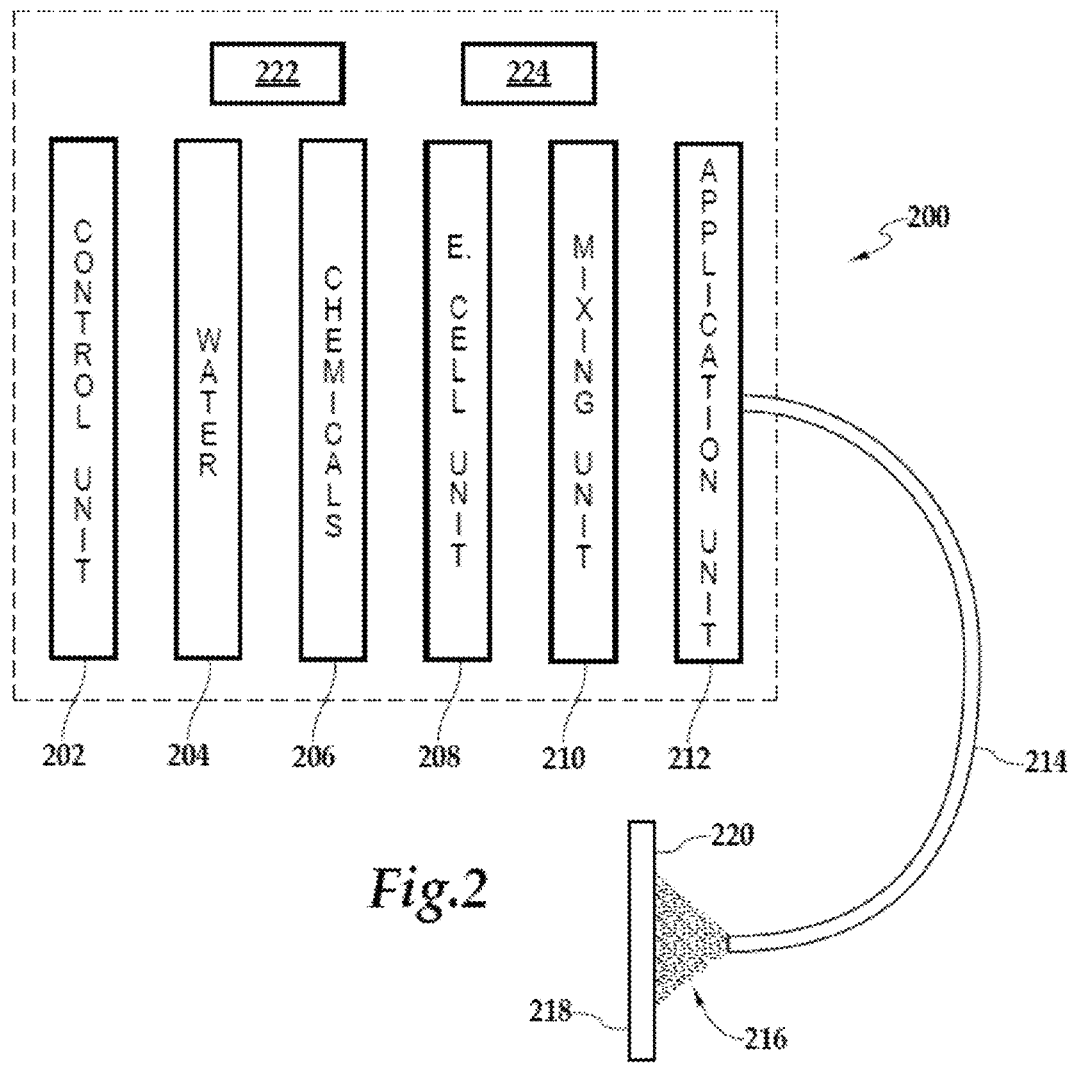
*Fig.2*
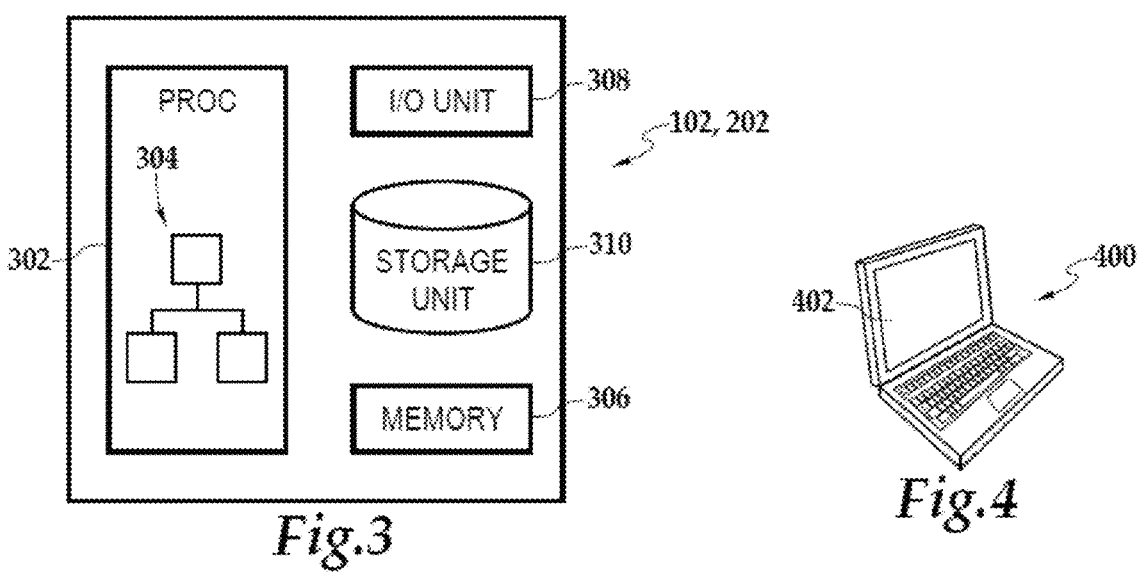
*Fig.3*     *Fig.4*

ELECTROLYTIC SYSTEM AND METHOD FOR GENERATING BIOCIDES HAVING AN ELECTRON DEFICIENT CARRIER FLUID AND CHLORINE DIOXIDE

CROSS-REFERENCE TO RELATED APPLICATIONS

This application is a continuation-in-part of prior U.S. patent application Ser. No. 12/947,818, filed Nov. 16, 2010, now U.S. Pat. No. 8,394,253, entitled "Electrolytic system ad method for generating biocides having an electron deficient carrier fluid and chlorine dioxide." The entirety of this aforementioned application is incorporated herein by reference.

TECHNICAL FIELD OF THE INVENTION

This invention relates to the generation of a biocide, and more particularly to an electrolytic system and method for generating biocides having an electron deficient carrier fluid and chlorine dioxide.

BACKGROUND OF THE INVENTION

Without limiting the scope of the present invention, its background will be described in relation to an electrolytic system and method for generating biocides having an electron deficient carrier fluid and chlorine dioxide, as an example.

The occurrence of secondary, facility-acquired infections is now a leading cause of preventable deaths in health care facilities worldwide. Conventional housekeeping and disinfecting formulations, procedures and practices are ill-equipped to provide effective biological decontamination of medical facilities and other public places. The inability to effectively decontaminate the physical plant of these varied facilities creates an environment that enables the rapid spread and mutation of pathogenic microbes.

Up to the present time, disinfection and decontamination of health care and other public facilities has been accomplished with various conventional disinfecting formulations, including quaternary ammonium formulas, phenolics, and various oxide materials such as peroxides, peracetics, hypochlorites, and chlorine dioxide formulations, among others. Over time, microbes have mutated, developing resistance to, and in some reported instances have begun to utilize some of these disinfecting formulations as a food source. These include many quaternary ammonium formulas and phenolic compounds, which represent a large proportion of disinfecting formulas currently in use. At the same time, common oxide-based materials are often toxic to humans, have significant adverse environmental impacts, are highly corrosive and harmful to equipment and many other common surfaces, and have other adverse effects on materials, substrates, and often worker health.

Conventional chlorine dioxide formulations have a number of drawbacks when considered for disinfectant use in active medical facilities. While gaseous-phase chlorine dioxide has seen considerable amounts of use as a decontaminant for biological incidents, this process cannot be used in functioning facilities due to factors that include material concentration and toxicity, corrosiveness of the disinfectant and the need to tightly maintain both temperature and humidity in order for the process to work effectively. Traditional chlorine dioxide solutions also possess many of the same drawbacks for wide area facility use. Historically, liquid/aqueous based chlorine dioxide solutions have had limited shelf life characteristics, normally lasting for hours to at most a day or two.

An exception to this fact are the "stabilized" chlorine dioxide products, which chemically are chlorite salts dissolved in water, where a low percentage of the chlorite salt content disassociates in the water, creating a weaker, lower quality chlorine dioxide solution. In order to achieve even a moderately effective level of chlorine dioxide in the solution, significantly higher chlorite salt contents are required to overcome the low level of disassociation of the chlorine dioxide from the chlorite salt, resulting in higher levels of corrosion, health hazards and effluent salt loading. Often, additional biocide products such as quaternary ammonium compounds are added to the formulations in order to enhance efficacy against microbes and to overcome the low level of chlorite salt disassociation.

Historic methods for the generation of chlorine dioxide solutions include passing a chlorite brine solution through an electrolytic cell to release chlorine dioxide from the chlorite salt, simple acid release processes where an acid solution is added directly to chlorite brine, and chlorine gas-based processes, among others. These generation methods have technical process shortcomings and drawbacks typical of conventional chlorine dioxide solutions, including limited shelf life, limited efficacy, high corrosiveness, low material compatibility, explosive hazards, higher human and animal toxicity, and significantly contaminated effluent products. These issues have previously hindered the widespread application of chlorine dioxide-based formulas for biological disinfection of medical and other public facilities.

Historical processes based on the mass production, packaging, storing, shipping, and distribution of disinfectant solutions has not lent itself to the production and use of top-quality, premium solutions that are required to stem the rising tide of microbial infections. Without exception, there has been no single solution that is highly effective, environmentally benign, non-toxic and materially compatible with substrates commonly found in health care and public facilities.

Additionally, another historical shortcoming of chlorine dioxide-based formulas has been the corrosivity of the powerful oxidizing solutions, which severely constrains the utility of the product. Chlorine dioxide solutions are known to be very aggressive against metallic surfaces and other sensitive substrates.

SUMMARY OF THE INVENTION

The above-described problems are solved and a technical advance achieved in the field by the present electrolytic system and method for generating biocides having an electron deficient carrier fluid and chlorine dioxide (termed "electrolytic chlorine dioxide biocide generation system" herein), which overcomes these problems by generating an electrolytic chlorine dioxide biocide that is highly oxidative, synergistically combining multiple pathogen killing mechanisms into one product.

In one embodiment, the present invention is directed to a system for electrolytically generating a biocide having an electron deficient carrier fluid and chlorine dioxide, including a feedstock vessel for containing a carrier fluid; at least one electrolytic cell in fluid communication with the feedstock vessel, the electrolytic cell having a semi-permeable membrane disposed therein defining an anodic chamber and a cathodic chamber; an anode electrode disposed in the anodic chamber for producing a oxidative acidic fluid and at least one acidic gas, and a cathode electrode disposed in the cathodic chamber for producing a reductive alkaline fluid; a power supply in electrical communication with the anode electrode and the cathode electrode; a mixing unit in fluid communication with the at least one electrolytic cell for mixing the oxidative acidic fluid, reductive alkaline fluid, and the at least one acidic gas to generate the biocide; and a control unit in communication with the feedstock vessel, the electrolytic cell, the power supply, and the mixing unit for controlling the operations of the feedstock vessel, the electrolytic cell, the power supply, and the mixing unit.

In one aspect, the at least one at least one electrolytic cell may be in series and/or the at least one at least one electrolytic cell are in parallel. In another aspect, the power supply may provide a pulse width modulation duty cycle to the anode electrode and the cathode electrode. In yet another aspect, the feedstock vessel includes a capacitive proximity sensor in communication with the control unit and disposed within the feedstock vessel that is operated when the gas volume within the feedstock vessel meets a threshold level. In still yet another aspect, the feedstock vessel may further include an orifice valve in communication with the capacitive proximity sensor, the orifice valve pulse width modulated for predetermined amounts of time to provide on/off cycles to the control unit. Also, the control unit may be configured to provide indirect gas volume measurements within the feedstock vessel based on the outputs of the orifice valve and pressure measurements within the feedstock vessel.

In another embodiment, the present invention is directed to a method for electrolytically generating a biocide having an electron deficient carrier fluid and chlorine dioxide, including providing a brine solution; providing a pair of electrodes interposed by a permeable membrane within a vessel for creating a first passageway and a second passageway, an anode electrode of the pair of electrodes disposed in the first passageway and a cathode electrode of the pair of electrodes disposed in the second passageway; flowing the carrier fluid through the vessel; applying an electric potential to the pair of electrodes to produce an anolyte fluid, an anolyte gas, a catholyte fluid, and a catholyte gas in the vessel; removing the anolyte fluid, the anolyte gas, the catholyte fluid, and the catholyte gas from the vessel; mixing a portion of the anolyte gas with the catholyte fluid to produce an ozone gas and hypochlorite bleach mixture; re-circulating a portion of the ozone gas with the ozone gas and hypochlorite bleach mixture to produce to shift the fluid ORP to more oxidative (+mV); mixing a portion of the anolyte fluid with the hypochlorite bleach solution; mixing a chlorite brine with the hypochlorite bleach solution to produce a chlorite brine/hypochlorite bleach solution mixture; and mixing a portion of the anolyte fluid with the chlorite brine/hypochlorite bleach solution mixture to the produce the biocide.

In one aspect, the providing a brine solution may include flowing a water source through an ion exchange water softener to remove contaminants and to provide sodium chloride to produce the brine solution. In another aspect, the method may further include determining the resonance time through the ion exchange water softener by monitoring the conductivity of the brine solution outflow. In yet another aspect, the method may include monitoring the pressure of the brine solution to the vessel for providing a desired volume of brine solution in the vessel. Also the method may include supplying the electric potential from one or more of a DC voltage power supply and battery banks. Additionally, the applying an electric potential may further include switching and structuring the electric potential with an H-bridge configured quadruplet solid state relay.

In still yet another aspect, the method may include controlling the H-bridge configured quadruplet solid state relay with a programmable logic controller for delivering the electric potential in varying polarity and pulse width modulation. Further, the method may include flowing the anolyte fluid and anolyte gas from the vessel to a second vessel having sufficient headspace for phase separation of the anolyte gas above the anolyte fluid. Also, the mixing a portion of the anolyte gas with the catholyte fluid may include aerating the catholyte fluid with the anolyte gas from in the second vessel.

In another aspect, the monitoring may further include monitoring at least one of pH and ORP of the oxidative acidic fluid and the reductive alkaline fluid. Further, the method may include adjusting the mineral content of the brine fluid. Also, the method may be a batch process and/or a continuous process.

BRIEF DESCRIPTION OF THE DRAWINGS

For a more complete understanding of the features and advantages of the electrolytic chlorine dioxide biocide generation system, reference is now made to the detailed description of the electrolytic chlorine dioxide biocide generation system along with the accompanying figures in which corresponding numerals in the different figures refer to corresponding parts and in which:

FIG. 2 is a block diagram of a portable electrolytic chlorine dioxide biocide generation system according to an embodiment of the present invention;

FIG. 3 is a block diagram of an exemplary control unit according to an embodiment of the present invention;

FIG. 4 is an illustration of an exemplary of computing device operating an exemplary control unit according to an embodiment of the present invention;

DETAILED DESCRIPTION OF THE INVENTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the present invention.

The described methods, processes, compositions, and systems described below may be performed by manual means, partial automated means, and/or fully-automated means, including manual, digital, and/or analog methods to monitor, process and control the electrolytic chlorine dioxide biocide generation system. While it is understood that the automation of these processes can be accomplished in a variety of ways by one skilled in engineering and system design, and with a complete understanding of the electrolytic chlorine dioxide biocide generation system, the description below provides description and use of a substantially automated technology.

Figure 1:
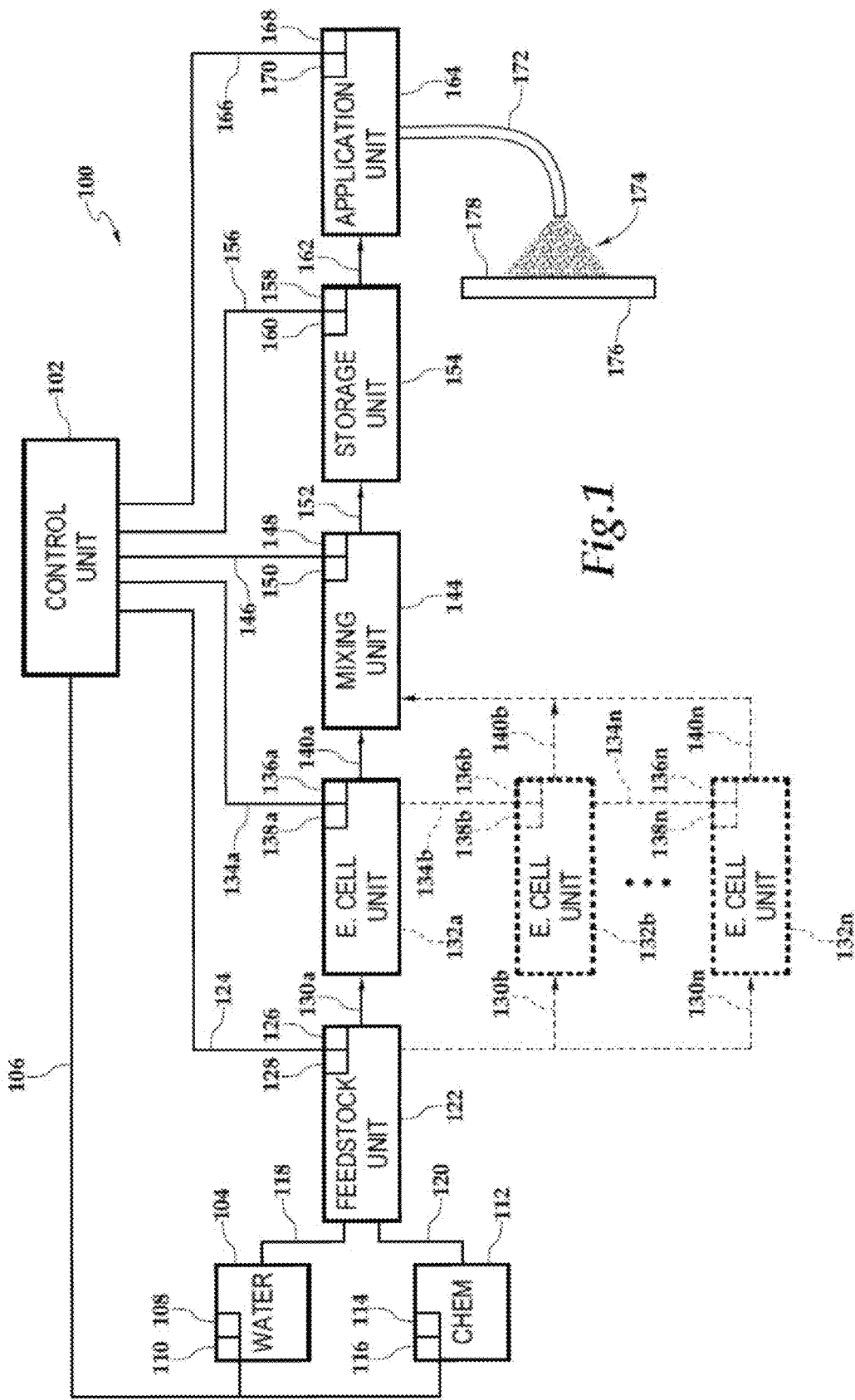
FIG. 1 is a block diagram of an electrolytic chlorine dioxide biocide generation system according to an embodiment of the present invention.

Referring to FIG. 1, an electrolytic chlorine dioxide biocide generation system is schematically illustrated and generally designated 100. Electrolytic chlorine dioxide biocide generation system 100 includes a control unit 102 in communication with a water source 104 via communication link 106. Water source 104 may include sensors 108 for determining the physical and/or chemical properties of the contents of water source 104. Additionally, water source 104 may include meters, valves and/or pumps 110 for monitoring and pumping water from water source 104 to feedstock unit 122 via conduit 118.

Electrolytic chlorine dioxide biocide generation system 100 may further include a chemical source 112 that is in communication with control unit 102 via communication link 106. Chemical source 112 may include sensors 114 for determining the physical and/or chemical properties of the contents of chemical source 112. Additionally, chemical source 112 may include meters, valves, and/or pumps 116 for monitoring and providing the feedstock chemicals to feedstock unit 122 via conduit 120.

Water source 104 is in fluid communication with a feedstock unit 122 via conduit 118. Additionally, chemical source 112 is in communication with feedstock unit 122 via conduit 120. Feedstock unit 122 may include sensors 126 for determining the physical and/or chemical properties of the brine solution of feedstock unit 122 produced by combining feedstock chemicals from chemical source 112 and water from water source 104. Additionally, feedstock unit 122 may include meters, valves, and/or pumps 128 for monitoring and providing the feedstock chemicals to feedstock unit 122 via conduit 120. Feedstock unit 122 is in communication with control unit 102 via communication link 124 for transmitting instructions, information, and data between sensors 126 and meters, valves, and/or pumps 128 of feedstock unit 122 and control unit 102 for controlling the operation of feedstock unit 122.

Electrolytic chlorine dioxide biocide generation system 100 may further include one of more electrolytic cell units 132a, 132b, 132n (collectively electrolytic cell units 132). Electrolytic cell units 132 are in fluid communication with feedstock unit 122 via conduits 130a, 130b, 130n, respectively (collectively conduits 130). Electrolytic cell units 132 may include sensors 136a, 136b, 136n, respectively, (collectively sensors 136) for determining the physical and/or chemical properties of the fluids in electrolytic cell units 132. Additionally, electrolytic cell units 132 may include meters, valves, and/or pumps 138a, 138b, 138n, respectively, (collectively meters, valves, and/or pumps 138) for monitoring and providing the fluid flow through electrolytic cell units 132. Electrolytic cell units 132 provide the electrolytic reactions of electrolytic chlorine dioxide biocide generation system 100 as further described below with reference to FIG. 10. Electrolytic cell units 132 are in communication with control unit 102 via communication links 134a, 134b, 134n, respectively, (collectively communication links 134) for transmitting instructions, information, and data between sensors 136 and meters, valves, and/or pumps 138 of electrolytic cell units 132 and control unit 102 for controlling the operation of electrolytic cell units 132.

As shown in FIG. 1, electrolytic cell units 132 may be in a parallel arrangement each receiving fluid and/or liquid feedstock from feedstock unit 122. In another embodiment, electrolytic cell units 132 may be in series, such that the output of one electrolytic cell unit 132 feeds the input of a subsequent electrolytic cell unit 132.

The output from electrolytic cell units 132 is fed to a mixing unit 144 via conduits 140a, 140b, 140n, respectively, (collectively conduits 140). Mixing unit 144 may include sensors 148 for determining the physical and/or chemical properties of the fluids in mixing unit 144. Additionally, mixing unit 144 may include meters, valves, and/or pumps 150 for monitoring and providing the fluid flow through mixing unit 144 to a storage unit 154 via conduit 152. Mixing unit 144 is in communication with control unit 102 via communication link 146 for transmitting instructions, information, and data between sensors 148 and meters, valves, and/or pumps 150 of mixing unit 144 and control unit 102 for controlling the operation of mixing unit 144. Once mixed, including the inclusion of any additives, the electrolytic chlorine dioxide biocides may be stored as described further herein. In general, the electrolytic chlorine dioxide biocides at this point are a biocide relying on the combined and synergistic effect of an oxidizing biocide using a carrier fluid with an engineered charge potential that is highly deficient in electrons, for example.

Storage unit 154 may include sensors 158 for determining the physical and/or chemical properties of the fluids in storage unit 154. Storage unit 154 may include meters, valves, and/or pumps 160 for monitoring and providing the fluid flow through storage unit 154 to an application unit 168 via conduit 162. Storage unit 154 is in communication with control unit 102 via communication link 156 for transmitting instructions, information, and data between sensors 158 and meters, valves, and/or pumps 160 of storage unit 154 and control unit 102 for controlling the operation of storage unit 154.

Electrolytic chlorine dioxide biocide generation system 100 may further include an application unit 164 that is in fluid communication with storage unit 154. Application unit 164 may include sensors 168 for determining the physical and/or chemical properties of the fluids in application unit 164. Application unit 164 may include meters, valves, and/or pumps 170 for monitoring and providing the fluid flow through application unit 164 to an applicator 172.

Applicator 172 may include several discharge devices, such as nozzles and the like for applying, spraying, depositing, etc. electrolytic chlorine dioxide biocide 174 onto a surface 178 of a material and/or object 176.

Turning now to FIG. 2, a portable electrolytic chlorine dioxide biocide generation system is schematically illustrated and generally designated 200. Portable electrolytic chlorine dioxide biocide generation system 200 may be any type of portable platform, such as backpacks, vehicles, trailers, and the like. Portable electrolytic chlorine dioxide biocide generation system 200 includes a control unit 202 that controls the other units in portable electrolytic chlorine dioxide biocide generation system 200.

Portable electrolytic chlorine dioxide biocide generation system 200 also includes a water source 204 for providing water to combine with a chemical source 206 for producing a brine solution that is fed to an electrolytic cell unit 208. Portable electrolytic chlorine dioxide biocide generation system 200 may also include a mixing unit 210 for mixing the products from electrolytic cell unit 208 as further described below. Also, portable electrolytic chlorine dioxide biocide generation system 200 may include an application unit 212 that may include an applicator 214 for spraying, applying, depositing, etc. electrolytic chlorine dioxide biocide 216 onto a surface 220 of a material and/or object 218.

In one aspect, portable electrolytic chlorine dioxide biocide generation system 200 may further include a feedstock unit (not shown) for combining the feedstock chemicals from chemical source 206 and water from water source 204 to provide a specific brine solution to electrolytic cell unit 208. In another aspect, portable electrolytic chlorine dioxide biocide generation system 200 may not include a feedstock unit, and the brine solution may be mixed dynamically from water source 204 and chemical source 206.

Additionally, portable electrolytic chlorine dioxide biocide generation system 200 may include sensors 222 for determining the physical and/or chemical properties of any or all of water source 204, chemical source 206, electrolytic cell unit 208, mixing unit 210, application unit 212, and applicator 214. Additionally, portable electrolytic chlorine dioxide biocide generation system 200 may include meters, valves and/or pumps 224 for monitoring and pumping water for any or all of water source 204, chemical source 206, electrolytic cell unit 208, mixing unit 210, application unit 212, and applicator 214.

In one aspect, water sources 104, 204 may be vessels, containers, and the like for storing a supply of water. In another aspect, water sources 104, 204 may be supplies of water, such as public water supplies, lakes, streams, etc. The physical and chemical properties of water source 104 may be measured or sensed during intake, storage, etc. for determining these properties for composition makeup. Additionally, these properties may be used in defining the extraction objectives and the field parameters. Some of these properties may be fluid total dissolved solids, mineral composition, etc.

In one embodiment, water sources 104, 204 may be portable sources of water that are carried or transported conveniently. They may be pre-filled containers, or containers that are filled at local water supplies and then transported to another location for operating electrolytic chlorine dioxide biocide generation system 100 and portable electrolytic chlorine dioxide biocide generation system 200, for example.

The chemicals and compounds that are stored in chemical sources 112, 206 are preferably any soluble chloride salt. Some exemplary chemicals stored in chemical sources 112, 206 may be sodium chloride, potassium chloride, lithium chloride, rubidium chloride, cesium chloride, ammonium chloride, magnesium chloride, calcium chloride, potassium nitrate, sodium nitrate, sodium phosphate, potassium phosphate, sodium sulfate, potassium sulfate, borate salts, or other applicable salts and the like.

In one embodiment, chemical sources 112, 206 may be substantially dry compounds that are then mixed with water to substantially near the solubility limit of the salt solution. In another embodiment, chemical sources 112, 206 may be substantially dry compounds that are then mixed with water at any limit below their solubility limits. Additionally, concentrated liquid chemical sources 112, 206 may also be used in these sources.

In general, the feedstock brine solution 1022 may be water, brine, or other fluid substance that can be treated and introduced to alter the electrochemical state of the liquid-solid interface. As described below, the chemical sources 112, 206 are mixed or combined with the water sources 104, 204, respectively, to produce a brine solution of a desired concentration. In one aspect, the brine solution concentration may be from approximately few parts per million ("ppm") to the saturation limit of the carrier fluid feedstock. In one embodiment, feedstock brine solution 1022 may have a concentration of chloride containing compound from about 1 ppm to about 15% w/w based on the total weight of feedstock brine solution 1022. Preferably, feedstock brine solution 1022 may have a concentration of chloride containing compound of from about 0.1% to about 10% w/w based on the total weight of feedstock brine solution 1022. In still yet another embodiment, feedstock brine solution 1022 may have concentration of chloride containing compound of from about 0.2% to about 0.7% w/w based on the total weight of feedstock brine solution 1022.

Generally, feedstock brine solution 1022 may be used at concentrations that vary from a few parts per million to well over 10%, depending on the specific application. The feedstock chemicals or salts are dissolved at specified rates in water to create a brine solution, with or without water filtering, softening, and other pre-treatment to remove unwanted constituents. Additionally, nano-particles (natural or man-made) or other suitable materials can be used or added to feedstock brine solution 1022 to enhance its ability to retain/carry a charge or otherwise enhance the carrying capacity or potential work capacity of the fluids.

As described herein, electrolytic cell units 132, 208 create the initial precursor acids and bases for the generation of the electrolytic chlorine dioxide biocide formulations. Hydroxides such as NaOH and KOH can be derived from their base salts. The conjugate hypochlorous/hydrochloric acids are also made from these salts. The oxidation/reduction potential ("ORP") of these fluids should be in the range of a few millivolts (mV) to over +/−1150 mV, depending on the chosen device settings, power supplies, applications, and formulary specifications. Electrolytic cell units 132, 208 are used for generating chlorine dioxide, where the chlorite salt ($NaClO_2$ or similar) does not pass through the electrolytic cell units 132, 208. By utilizing the produced fluids in the generation of the biocide compositions, the ORP is maintained in the compositions, providing an additional important microbial kill mechanism.

In addition, the cell life of electrolytic cell units 132, 208 may be enhanced by, in a certain embodiment, solid state modulation of reactor electricity and polarity for self cleaning of the surfaces and pores of semi-permeable membrane 1008, anode electrode 1004 and cathode electrode 1006. The modulation of the electrical supply and the acid and alkaline streams may be used to dissolve scale formation in-situ in order to both optimize electrolytic component life and optimize formulary potency.

Additionally, mixing units 144, 210 may further include supplies of additives for mixing with the electrolytic chlorine dioxide biocides solutions from electrolytic cell units 132, 208. The unique additives that are tolerant of the highly oxidative formulation assist as wetting agents and micelle generators, while reducing corrosion at near neutral pH levels. Although the supply of additives is described herein with reference to mixing units 144, 210, all or any of the other units described herein may also include this or other supplies of additives to be added to the electrolytic chlorine dioxide biocides produced in electrolytic cell units 132, 208.

Some exemplary additives may include: buffers, surfactants, chelants, or other enhancing materials. Some additional additives include buffers for buffering the electrolytic chlorine dioxide biocides to the desired pH, using any of a wide range of buffering materials, such as but not limited to, carbonates, bicarbonates, or similar.

Some of these additives may be surfactants, which may be any compound or combination of compounds that assists in lowering surface tension, increasing wettability, creating micelles or adding detergent effects to the fluid that assists in decontamination applications.

The surfactants may be added at a rate of 0.001% to over several percent depending on specific application. The surfactants typically include alcohol ethoxylates, alkyl sulfates and lauroyl sarcosinates. These include but are not limited to Stepan's Bio-Soft series, Ammonyx series, Bio-Terge series, Stepanol series, Air Products Tomodol series, and Croda's Crodasinic LS-30 or similar surfactants that are tolerant of oxidizing and reducing solutions. In most cases, EPA certified Designed for Environment (DFE) surfactants are preferred, but not required.

The integrated sensors 108, 114, 126, 136, 148, 158, 168, 222 of electrolytic chlorine dioxide biocide generation system 100 and portable electrolytic chlorine dioxide biocide generation system 200 provide for continuous monitoring of output concentrations within specifications, and notification of operator of any variances in order to assure product quality. Other benefits include totalizing capability on both produced electrolytic streams and on produced compositions and formularies.

Sensors 108, 114, 126, 136, 148, 158, 168, 222 may be the types of sensors that measure physical and/or chemical properties of the respective liquid, gas, and/or fluid in their respective environments. The measurements or data from sensors 108, 114, 126, 136, 148, 158, 168, 222 may be communicated to control units 102, 202 for adjusting any or all of the processes relating to electrolytic chlorine dioxide biocide generation system 100 and portable electrolytic chlorine dioxide biocide generation system 200, including controlling and adjusting the operation of meters, valves and/or pumps 110, 116, 128, 138, 150, 160, 170, 224. For example, sensors 108, 114, 126, 136, 148, 158, 168, 222 may measure in measuring key composition components, such as the reduction potential, redox potential, oxidation/reduction potential ("ORP") of the carrier fluid and pH of any of the liquids, fluids, and/or gases of any of the units described herein.

In one aspect, ORP means a quantitative measure of the energy of oxidation or reduction. Oxidation is equivalent to a net loss of electrons by the substance being oxidized, and reduction is equivalent to a net gain of electrons by the substance being reduced. The oxidation-reduction reaction involves a transfer of electrons. The oxidation-reduction potential may be expressed as the ability to give or receive electrons and is expressed in terms of millivolts (mV) which may be either positive (lack of electrons) or negative (excess of electrons).

In one aspect, control units 102, 202 analyze the data provided by sensors 108, 114, 126, 136, 148, 158, 168, 222 of electrolytic chlorine dioxide biocides 174, 216 by utilizing continuous monitoring of calculations, inferences, and/or indirect measurements of electrolytic components from combined values of electrolyte potential (i.e. composition & concentration), reactor current density, produced volume measurement of component gases, and direct liquid or fluid flows. Control units 102, 202 may provide real-time analysis of key parameters, chemical properties, and/or physical properties. This eliminates dependence on human calibrated monitoring devices that are prone to drifting out of specification and makes Quality Assurance of the generated electrolytic chlorine dioxide biocides 174, 216.

In one embodiment, control units 102, 202 of electrolytic chlorine dioxide biocide generation system 100 and portable electrolytic chlorine dioxide biocide generation system 200 may use any of the following examples to predict or determine pH values and ORP of any of the liquids, fluids, gases, etc. in these systems' units. In one example, control units 102, 202 may intake data from sensors that constantly or continuously monitor flow rates at the inlet and outlets of electrolytic cell units 132, 208. In another example, control units 102, 202 may intake data from sensors that constantly or continuously monitor the electrolyte composition and concentration within electrolytic cell units 132, 208.

In yet another example, control units 102, 202 may intake data from sensors that constantly or continuously monitor electrolyte pressure within electrolytic cell units 132, 208. In still yet another example, control units 102, 202 may intake data from sensors that constantly or continuously monitor the efficient separation of the gas phase from the liquid phase in outlet streams of electrolytic cell units 132, 208. Further, control units 102, 202 may intake data from sensors that constantly or continuously monitor or measure the post-separation gas volumes from electrolytic cell units 132, 208. Also, control units 102, 202 may intake data from sensors or electronics that constantly or continuously monitor or maintain DC voltage through electrolytic cell units 132, 208.

In one aspect, objects 176, 218 may be any types of objects or substrates. Additionally, surfaces 178, 220 may be any types of surfaces, including but not limited to: concrete, stone, tile, metal, asphalt, glass, plastic or various soft materials (fabrics or similar) that may become contaminated.

Now turning to FIG. 3, a block diagram of exemplary control units 102, 202 configured to perform functionality in accordance with the principles of electrolytic chlorine dioxide biocide generation systems 100, 200 is shown. Control units 102, 202 may include a processing unit 302 that includes one or more processors that execute software 304. In one embodiment, software 304 may include module(s) that operate to analyze the output data from sensors 108, 114, 126, 136, 148, 158, 168, 222. Processing unit 302 may be in communication with a memory 306 configured to store information, such as output data from sensors 108, 114, 126, 136, 148, 158, 168, 222, in registers or one or more tables in memory, as understood in the art. Processing unit 302 may further be in communication with an input/output ("I/O") unit 308 that is configured to communicate over one or more wired or wireless communication links. I/O unit 308 may include one or more access ports (not shown). Processing unit 302 may also be in communication with a storage unit 310 that is configured to store one or more data repositories (e.g., databases) that store performance information relating to electrolytic chlorine dioxide biocide generation system 100 and portable electrolytic chlorine dioxide biocide generation system 200. Storage unit 310 may work in conjunction with memory 306. These memory registers are sometimes referred to as bins.

In one embodiment, control units 102, 202 may be portable control units that are part of electrolytic chlorine dioxide biocide generation system 100 or portable electrolytic chlorine dioxide biocide generation system 200. These control units 102, 202 may be integral part of the units of electrolytic chlorine dioxide biocide generation system 100 and portable electrolytic chlorine dioxide biocide generation system 200 or they may be remote units that communicate via wired or wireless technology with the units of electrolytic chlorine dioxide biocide generation system 100 and portable electrolytic chlorine dioxide biocide generation system 200. Some exemplary embodiments of control units 102, 202 may include personal computers ("PCs") 400 (FIG. 4), laptops, network computers, wireless portable handheld devices, PDAs, smartphones, and the like.

Additionally, control units 102, 202 may communicate with sensors 108, 114, 126, 136, 148, 158, 168, 222 via wired or wireless communication protocols. Further, control units 102, 202 may communicate with meters, valves and/or pumps 110, 116, 128, 138, 150, 160, 170, 224 via wired or wireless communication protocols. Some exemplary wireless communication protocols may include radio frequency technologies, IEEE 802.1.115.1 Bluetooth protocols, IEEE 802.15.3 UWB protocols, IEEE 802.16d/802.16-2004 WIMAX Fixed Access protocols, CDMA One/2000 networks, GSM/GPRS/EDGE/WCDMA networks, IEEE 802.15.4 ZigBee protocols, IEEE 802.11 protocols, and the like.

This allows trained users to quickly produce and "fine tune" formulas specifically targeting the particular environment and situation at hand. Graphical user interfaces ("GUIs") (FIGS. 5-9) are displayed to a user by electrolytic chlorine dioxide biocide generation system 100 and portable electrolytic chlorine dioxide biocide generation system 200 providing them with display information and selection inputs for controlling electrolytic chlorine dioxide biocide generation system 100 and portable electrolytic chlorine dioxide biocide generation system 200. These GUI displays may display information to a user relating to the operation and control of any or all of sensors 108, 114, 126, 136, 148, 158, 168, 222, and meters, valves and/or pumps 110, 116, 128, 138, 150, 160, 170, 224.

Figure 5:
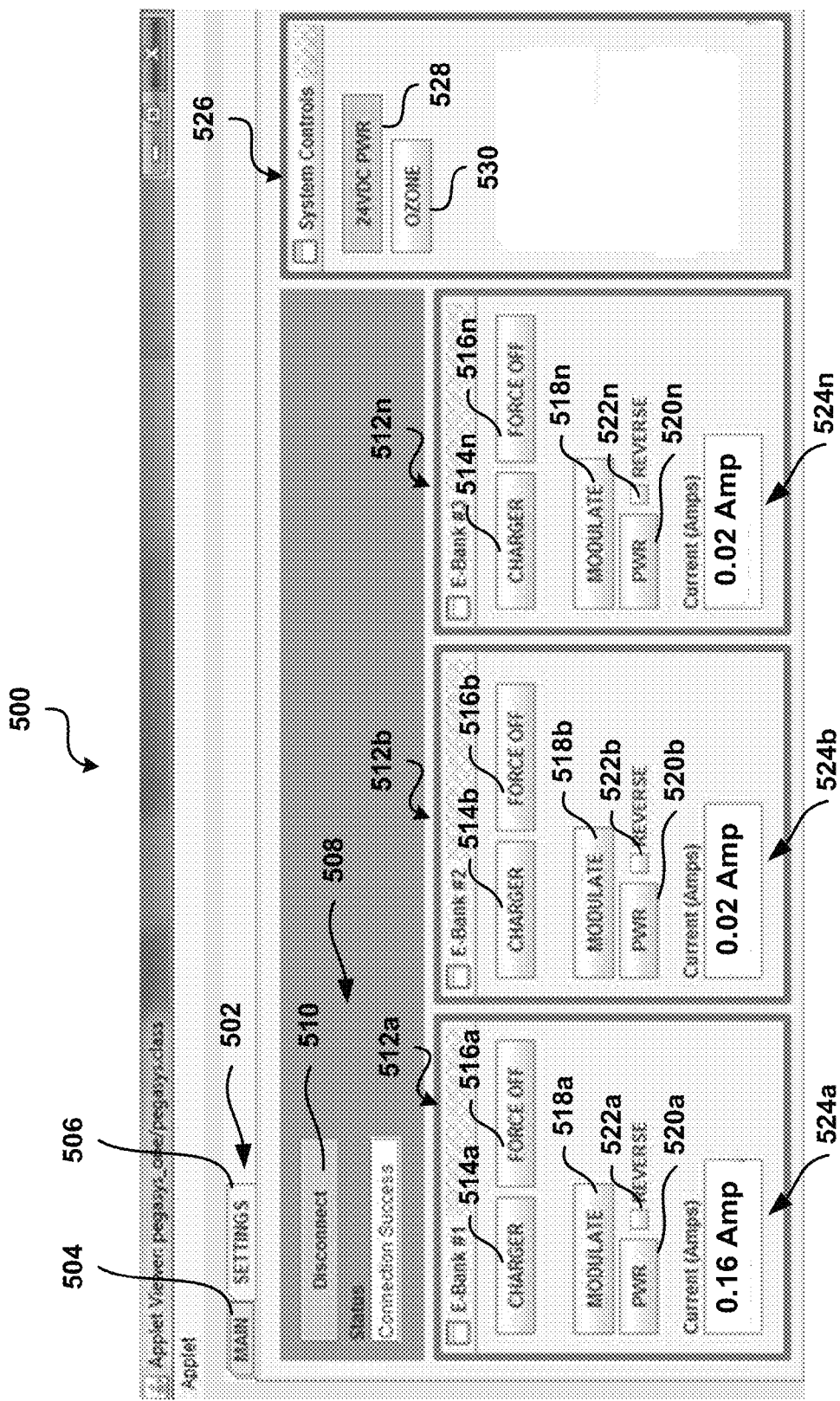
FIG. 5 is a screen shot of an exemplary graphical user interface of a electrolytic chlorine dioxide biocide generation system according to an embodiment of the present invention.
Figure 6:
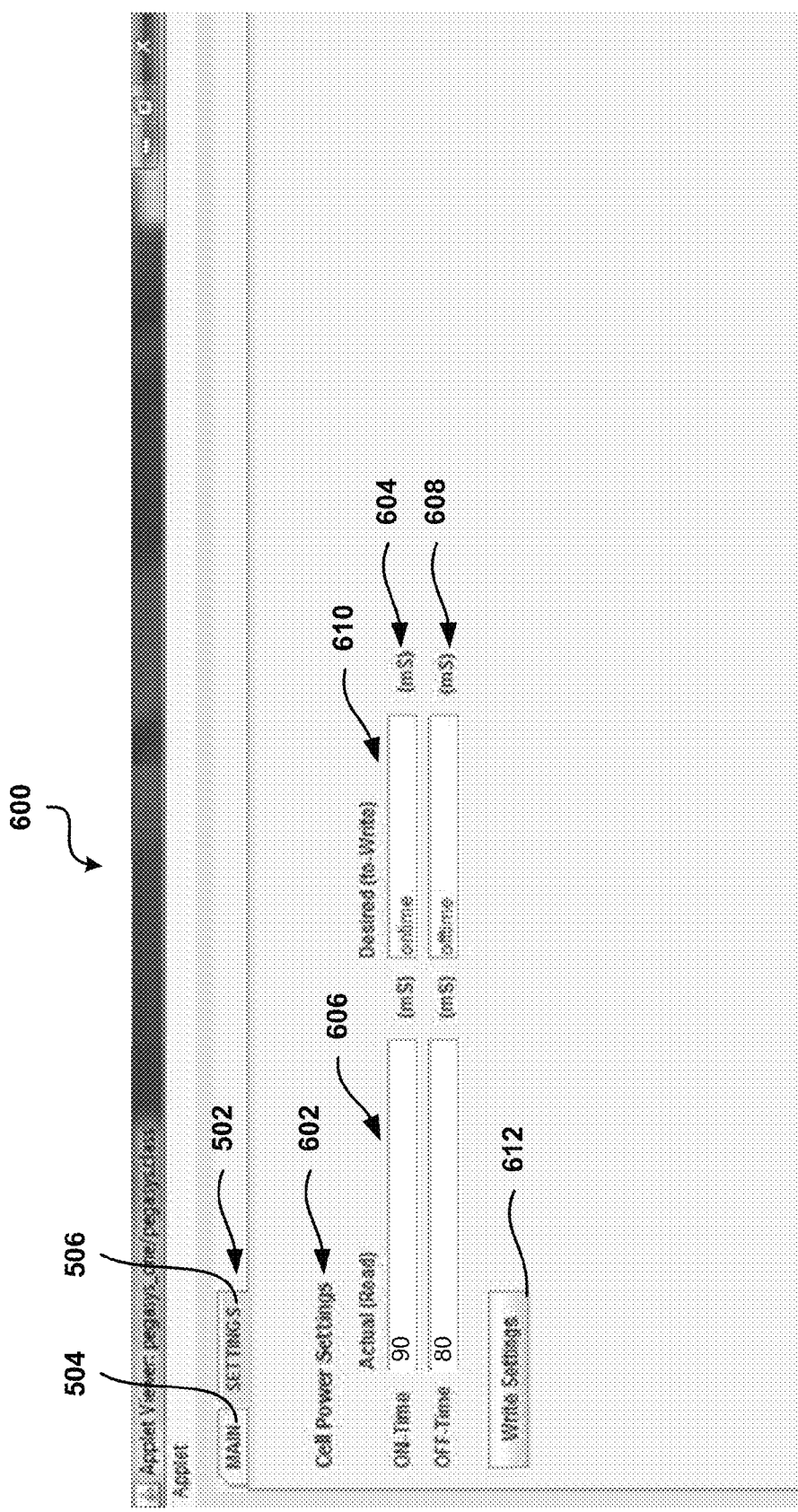
FIG. 6 is a screen shot of an exemplary graphical user interface of a electrolytic chlorine dioxide biocide generation system according to another embodiment of the present invention.

Turning now to FIGS. 5 and 6, screen shots of exemplary graphical user interfaces ("GUI") is generally shown and designated 500 and 600, respectively. GUI 500 may include a basic menu structure water source 502 that may be displayed to a user that displays additional interactive buttons or selections for the user to select, such as a main display 504 and a settings display 506. Additionally, main display 504 of GUI 500 may display a status information 508 to a user noting the connection status of the electrolytic chlorine dioxide biocide generation systems 100, 200 and a disconnect selector 510 for use by a user to disconnect the computing/software components of the electrolytic chlorine dioxide biocide generation systems 100, 200 from any hardware/electrolytic cells and the like. Further, main display 504 of GUI 500 may display to a user one or more electrolytic cells or electrolytic banks 512*a*-512*n* (collectively electrolytic banks 512) that include many controls for controlling electrolytic banks 512 individually or collectively. Electrolytic banks 512 may include a charger selector 514*a*-514*n* (collectively charger selector 514) and a force off selector 516*a*-516*n* (collectively force off selector 516) for use by a user.

Additionally, electrolytic banks 512 may include a modulate selector 518*a*-518*n* (collectively modulate selector 518) and a power selector 520*a*-520*n* (collectively power selector 520) for enabling a user to control the modulation and power to electrolytic cells or banks of electrolytic chlorine dioxide biocide generation systems 100, 200. Also, electrolytic banks 512 of main display 504 of GUI 500 may include a reverse selector 522*a*-522*n* (collectively reverse selector 522) for enabling a user to control the polarity of the current applied to the electrolytic cells or banks of electrolytic chlorine dioxide biocide generation systems 100, 200 as described herein. GUI 500 may further display to a user an current reading or measurement 524*a*-524*n* (collectively current measurement 524) that displays to the user the current measurement of each of the electrolytic banks 512. GUI 500 may also include a system controls display 526 that may display a power button 528 and an ozone button 530 to a user for controlling these parameters of electrolytic chlorine dioxide biocide generation systems 100, 200 as described herein.

Turning now to FIG. 6, a screen shot of another exemplary GUI is shown and generally designated 600. GUI 600 may display various settings, such as specific parameters of cell power settings 602. Some of the parameters may include the reading and writing times for the different components of the electrolytic chlorine dioxide biocide generation systems 100, 200. Cell power settings 602 may include an on-time 604 actual read value 606 and an off-time 608 actual read value 606. Additionally, cell power setting 602 may include an on-time 604 desired (to-write) value 610 and an off-time 608 desired (to-write) value 610. These write and read times may be adjusted by selecting a write settings button 612, in one example.

Figure 7:
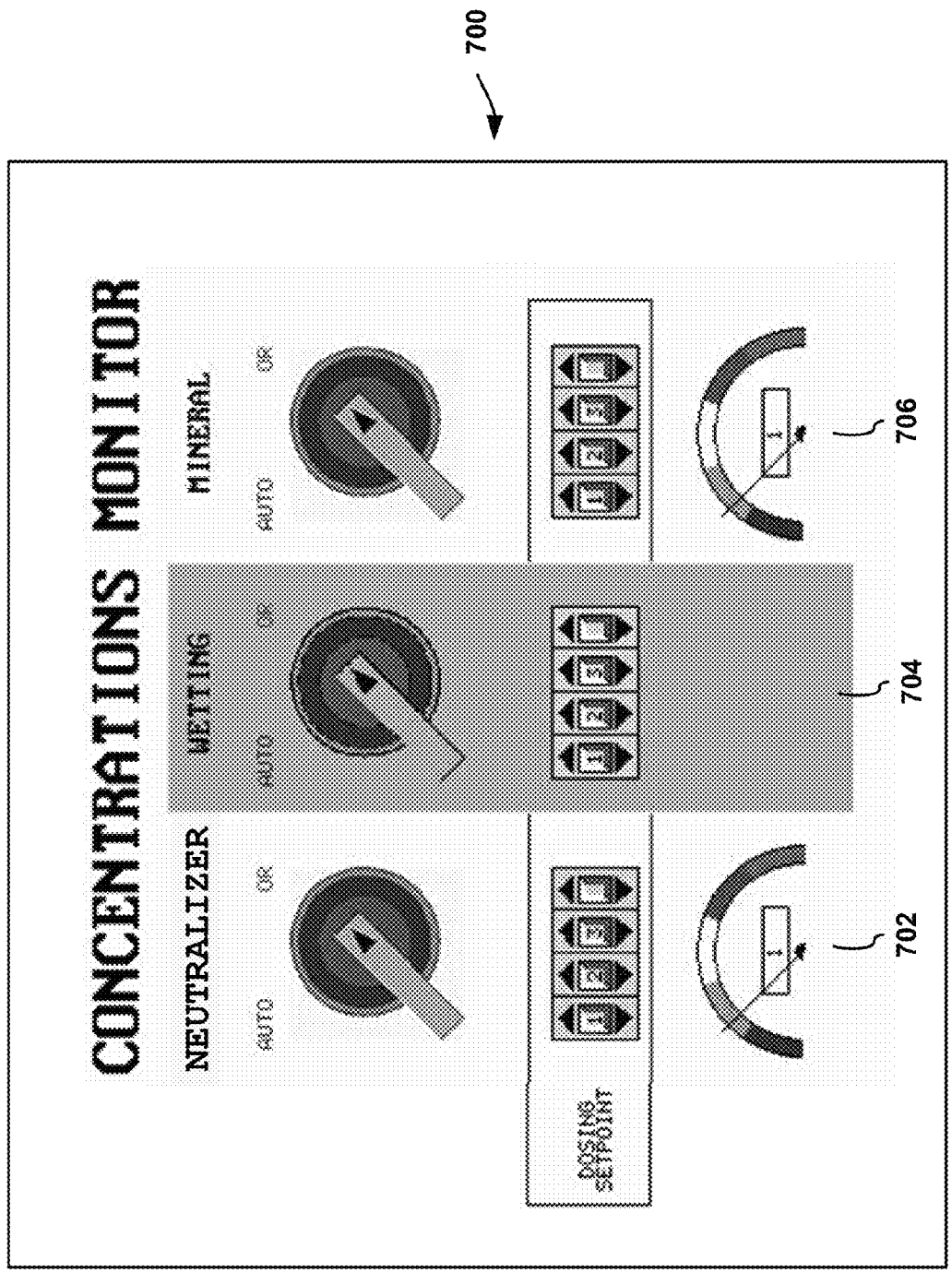
FIG. 7 is a screen shot of an exemplary graphical user interface of a electrolytic chlorine dioxide biocide generation system according to yet another embodiment of the present invention.

Turning now to FIG. 7, a screen shot of another exemplary GUI is shown and generally designated 700. GUI 700 may display various different monitor screens such as neutralizer 702, wetting 704, and mineral 706 to control a group of components or control loops. These monitors may be for dosed/metered in feedstocks. These monitors may be for monitoring an oxygenated salt or substitute nomenclature for sodium chlorite, for example, as well as the mineral or alternate nomenclature for sodium chloride are both PID/feedback controlled loops with dynamic controller adjustment of metered proportion state. The dial gages at the bottom of GUI 700 may be the sensed value. The neutralizer or buffering carbonate as well as the wetting or surfactant concentrates may be metered in at a preset concentration rate. GUI 700 may be for manual control of feedstock metering rates, for example. Systems may be taken out of automated control via the override setting.

Figure 8:
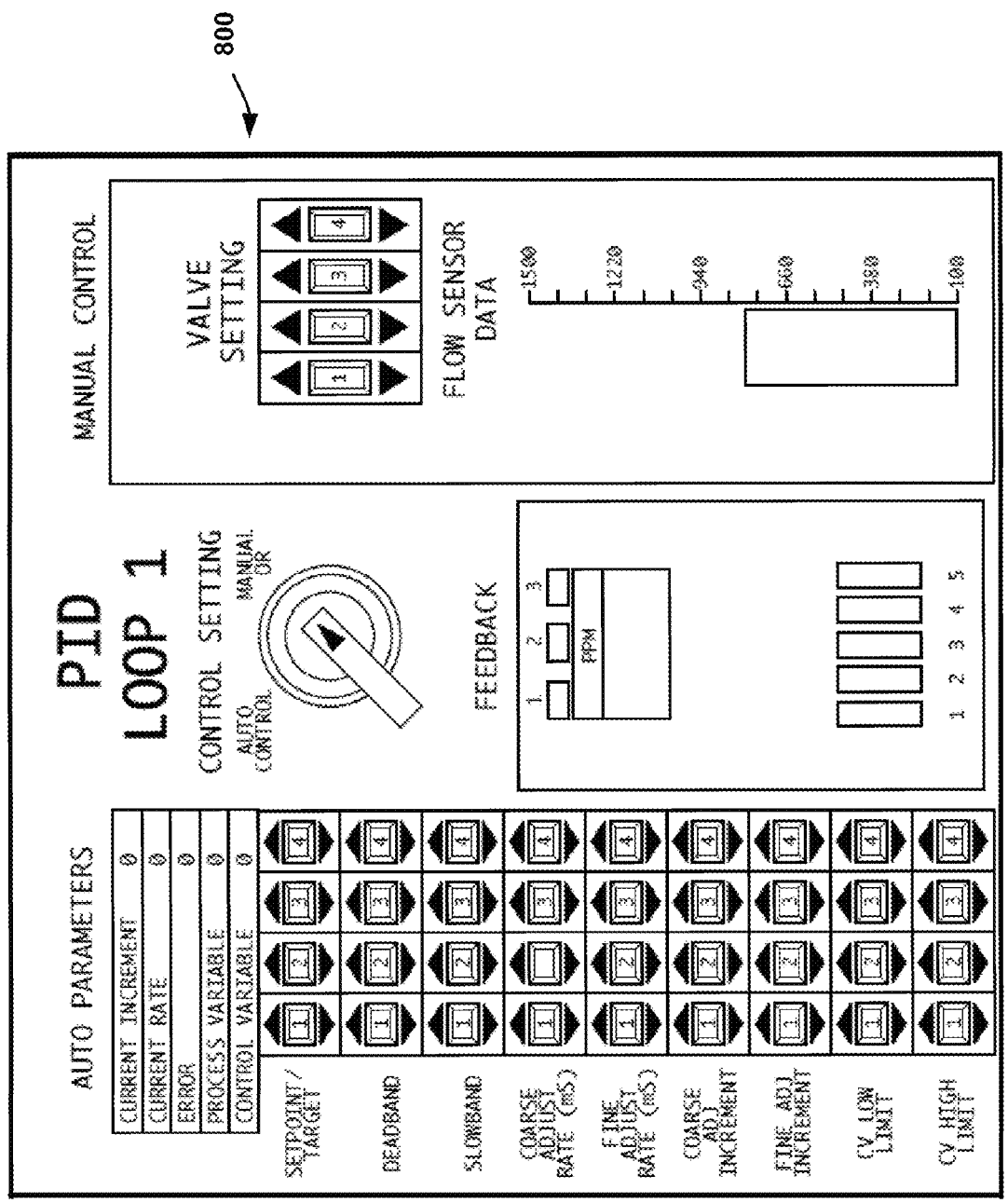
FIG. 8 is a screen shot of an exemplary graphical user interface of a electrolytic chlorine dioxide biocide generation system according to still yet another embodiment of the present invention.

With reference now to FIG. 8, a screen shot of still yet another GUI is shown and generally designated 800. GUI 800 may show one of a plurality of feedback control loops, each of which may control a stepped valve/flowmeter combination, a variable dosing pump/concentration sensor combination, and/or a stepped valve/pressure transducer combination as respective inputs and outputs. In one aspect, each loop may have various constants that impact control dynamics such as rate of change, variable delay, etc.

Figure 9:
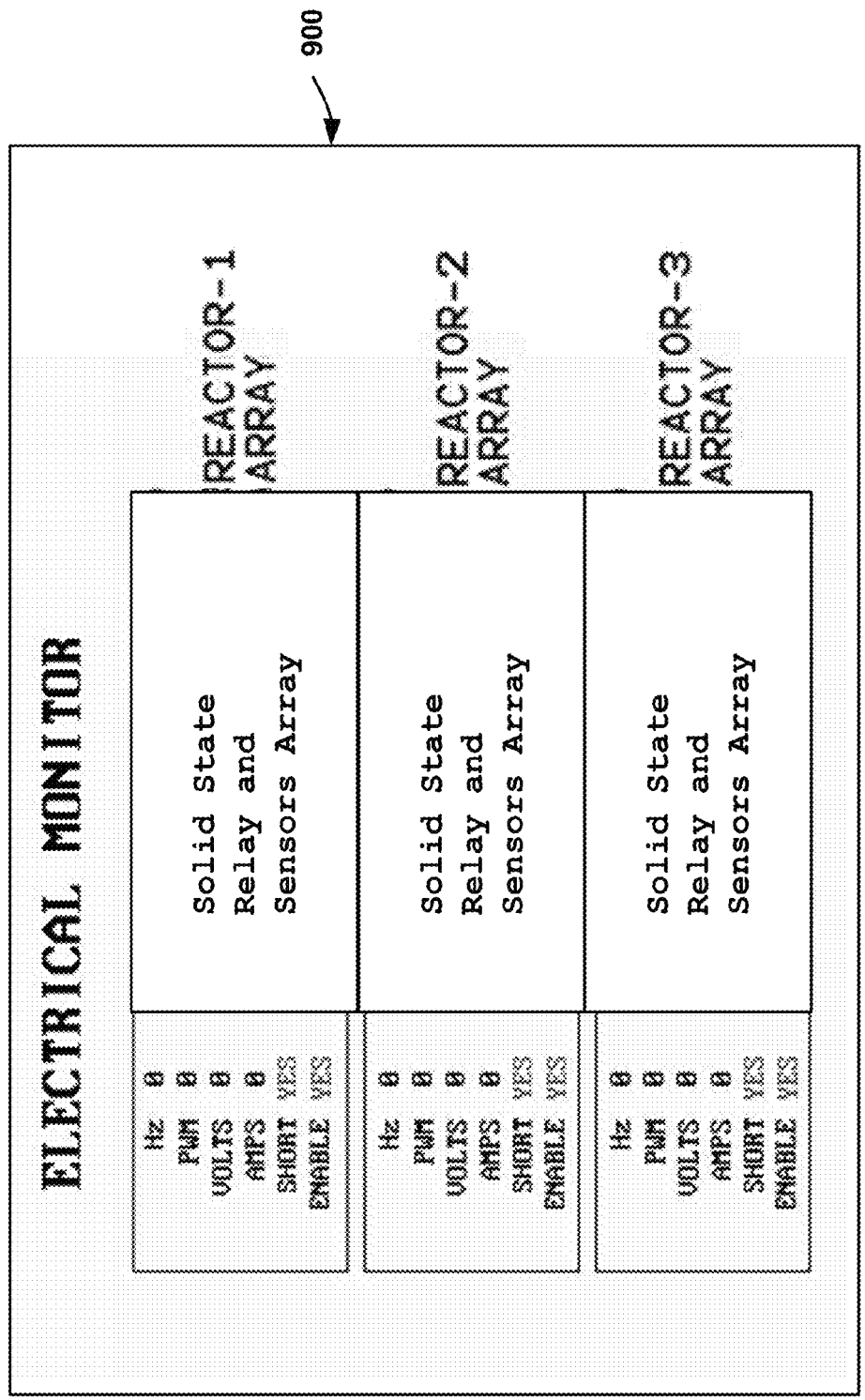
FIG. 9 is a screen shot of an exemplary graphical user interface of a electrolytic chlorine dioxide biocide generation system according to an embodiment of the present invention.

Turning now to FIG. 9, a screen shot of a GUI is shown and generally designated as 800. GUI 800 may display to a user status indication of unit electronic arrays comprised of H-bridge configured transistorized relays and solid-state sensing components that provide for current sensing, voltage sensing, PWM modulation of reactor supply, and variable frequency of reactor supply, for example. Each relay bridge may have a maximum capacity of a certain amount of current, such as meters, valves, and/or pumps of electrolytic chlorine dioxide biocide generation systems 100, 200 and a delayed short circuit detection and shutdown protection logic. In one example, the delay may be approximately 5 seconds. Additionally, a slower burn fuse may also be included as replacement or redundant protection.

Figure 10:
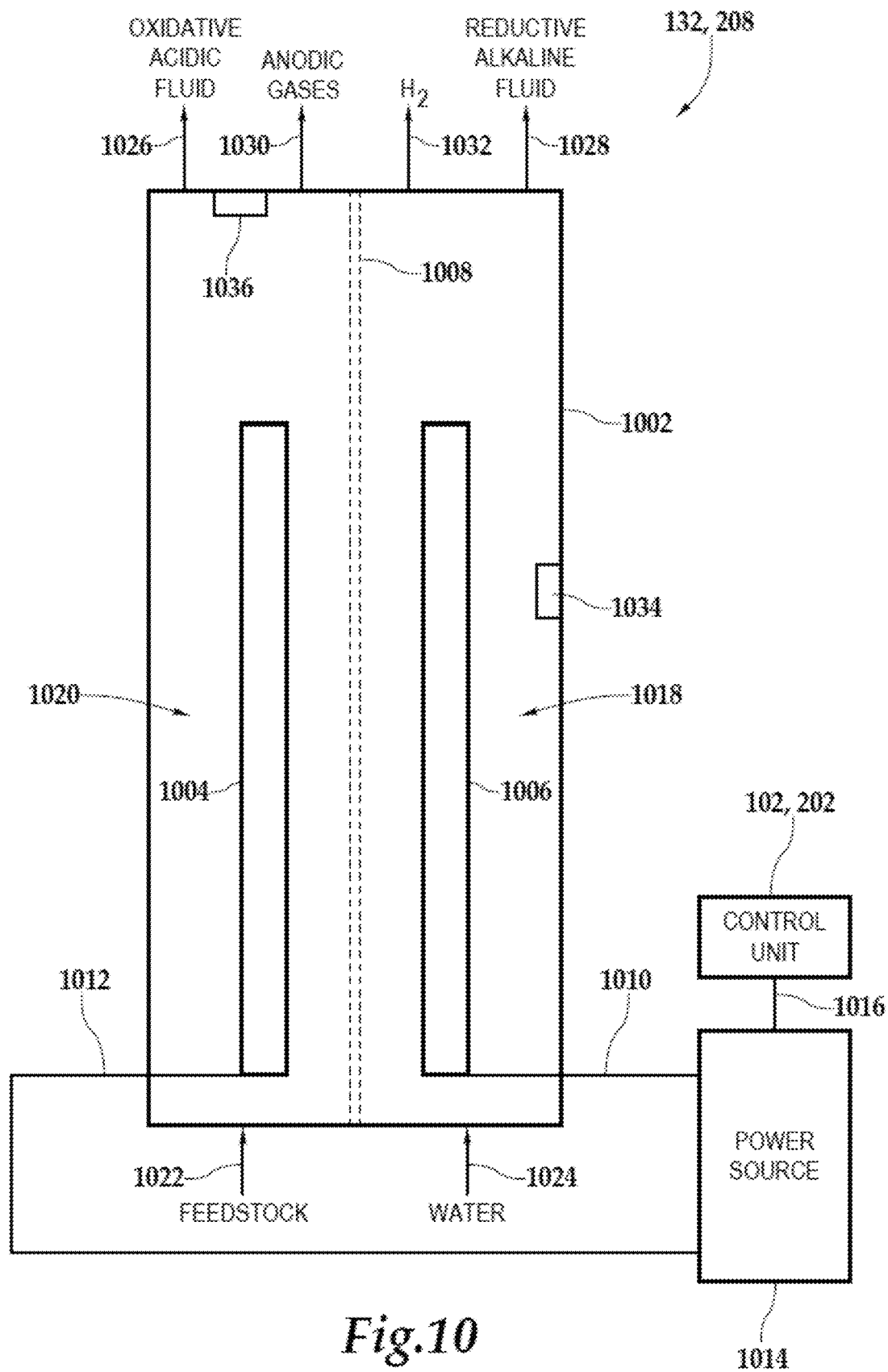
FIG. 10 illustrates a plan view of an electrolytic cell unit according to an embodiment of the present invention.

Referring now to FIG. 10, exemplary electrolytic cell units 132, 208 are shown. Electrolytic cell units 132, 208 ionize the brine solution or carrier fluid of electrolytic chlorine dioxide biocide generation system 100 and portable electrolytic chlorine dioxide biocide generation system 200. The generation of an ionized carrier fluid is produced by ionizing the carrier fluid in electrolytic cell units 132, 208. Electrolytic cell units 132, 208 typically include an insulated container, vessel, shell, and/or housing 1002 with a plurality or series of pairs of electrode plates, such as anode electrode 1004 and cathode electrode 1006. In some designs a conducting material may be used for the housing and then doubles as the electrodes. In one embodiment, anode electrode 1004 and cathode electrode 1006 are separated by a permeable or semi-permeable membrane 1008. An electrical potential or voltage is applied to anode electrode 1004 and cathode electrode 1006 via electrical leads 1010 and 1012 while a carrier fluid flows through electrolytic cell units 132, 208. Generally, the electrical potential or voltage is applied by a power source 1014 that is in communication with control units 102, 202 via communication link 1016.

In one embodiment, insulated housing 1002 may have an internal diameter of sufficient size that reduces the turbulence and flow velocity of the mixed gas/liquid phase stream as they flow through electrolytic cell units 132, 208. This provides or allows the buoyant vertical separation of gas and liquid phases with insulated housing 1002. In one embodiment, a capacitive proximity sensor 1034 positioned near the midpoint of the vertical vessel wall detects when the gas volume has grown to reach the sensor's switch point. Once the volume of gas in the vessel has exceeded the threshold level, a controlled, valve orifice 1036 is pulse modulated for predetermined amounts of time, normally on the order of milliseconds. The counting of on/off cycles of the orifice valve 1036 (i.e. duration of "on" time) along with pressure measurements within insulated housing 1002 of electrolytic cell units 132, 208 provides for indirect measurement of gas volumes. As the gas compositions may be different between a cathodic chamber or passageway 1018 and an anodic chamber or passageway 1020 sides of electrolytic cell units 132, 208, they are each directed to subsequent reaction positions further downstream.

This system provides for the accurate measurement of gas volumes and maintains consistent component contributions to the staged reactions used in the generation of the electrolytic chlorine dioxide biocide compositions, resulting in more consistent formulary generation through time.

Passageways 1018 and 1020 are created on each side of permeable membrane 1008. Cathode electrode 1006 is disposed within passageway 1018 and anode electrode 1004 is disposed within passageway 1020. The carrier fluid produced by combining water with the feedstock chemicals as further described below produces a feedstock brine solution 1022 that is supplied to passageway 1020 that acts as the conducting medium between anode electrode 1004 and cathode electrode 1006. Additionally, a supply of water 1024 is provided to passageway 1018. The charge across anode electrode 1004 and cathode electrode 1006 causes anions to be attracted to anode electrode 1004 and cations to be attracted to the cathode electrode 1006. Thus, the ionized carrier fluid is oxidized at the anode electrode 1004 producing an oxidative acidic fluid 1026 and the ionized carrier fluid is reduced at the cathode electrode 1006 producing a reductive alkaline fluid 1028. Oxidative acidic fluid 1026 in passageway 1020 is oxidized and reductive alkaline fluid 1028 in passageway 1018 is reduced. Additionally, anodic gases 1030 are produced in passageway 1020 and are also exited out of electrolytic cell units 132, 208. Hydrogen gas 1032 is also generated in passageway 1018 and is also exited out of electrolytic cell units 132, 208. A basic ionizer may also be constructed by using simple containers (like tanks) with an electrode in each container and linked with a conduit separated by a membrane. In this "batch" approach a flowing fluid may not be necessary.

In general, electrolytic cell units 132, 208 have inlets (not shown) disposed in their bodies or housings for accepting the inputs or inlets of feedstock brine solution 1022 and water 1024. Further, electrolytic cell units 132, 208 have outlets (not shown) disposed in their bodies of housings for accepting the outputs or outlets of oxidative acidic fluid 1026, reductive alkaline fluid 1028, and anodic gases 1030, for example.

Additionally, permeable membrane 1008 may be any type of membrane that facilitates the flow of certain ions through the membrane as is commonly known to those skilled in the arts of electrolytic cells. In one embodiment, permeable membrane 1008 may be a GoreTex® SGT100120-1 (or similar) membrane material for ion transfer therethrough.

In one embodiment, control units 102, 202 of electrolytic chlorine dioxide biocide generation system 100 and portable electrolytic chlorine dioxide biocide generation system 200 operate with a dynamic process instrumentation diagram ("PID")-loop control of each component stream flow, dynamic trim adjustments are made to individual stream controls to maintain formula proportions. Expansion chambers, fluid transport tubes and/or vessels of varying diameters and internal volumes may be used to create engineered reaction resonance times and turbulence required for the optimization of the electrolytic chlorine dioxide biocide generation steps as described herein and below.

The ionization of feedstock brine solution 1022 that is saline (or other fluid with appropriate TDS) changes the fluid ionic composition on both sides of permeable membrane 1008. For example, as feedstock brine solution 1022 passes through electrolytic cell units 132, 208, it undergoes a partial disassociation of both the water (HOH) component and salt (NaCl) component, for example, of the carrier fluid, with ions migrating through permeable membrane 1008 to the opposite charged side where re-association will occur. For example, in passageway 1018 of permeable membrane 1008, sodium ions ($Na^+$) and hydroxyl ions ($OH^-$) will re-associate to form sodium hydroxide, NaOH, commonly known as the "alkaline" side to produce reductive alkaline fluid 1028. On the opposite charged side, passageway 1020, hydrogen ions ($H^+$) will re-associate with chlorine ($Cl^-$) and form hydrochloric acid, HCl or more typically hypochlorous acid, HOCl, and is often known as the "acidic" or astringent side to produce oxidative acidic fluid 1026. Other compounds or combinations of compounds are used to attain the same goals using this approach.

Both ionized materials will also have a significant "shift" in their respective redox potential from the initial state of the carrier fluid as the carrier fluid is adjusted to a different ionic state. The alkaline side will have a dramatic increase in excess electrons and become a powerful reducing agent. The opposite is true for the acidic side, which is deficient in electrons and is thus a powerful oxidizer. These shifts in redox potential can be well in excess of +/−1150 mV as measured by ORP. This limit can be as high as where the carrier fluid completely disassociates and will not carry any additional charge, or is no longer useful to the process. Alternatively, any measurable change in redox may be sufficient to produce desirable results. This measurement can be made by a simple pH/ORP meter or sensor or more sophisticated data logging can be achieved by using a continuous flow through design, such as with inline pH/ORP analyzers.

Some of the variables that control the magnitude of the electrolytic process are the flow rate of the carrier fluid through insulated housing 1002, the charge potential between anode electrode 1004 and cathode electrode 1006, the carrier fluid residence time, and the amperage used to ionize the carrier fluid. According to process designs, variables such as voltage and amperage applied to anode electrode 1004 and cathode electrode 1006, flow rate through passageway 1018 and passageway 1020, and/or brine concentration of feedstock brine solution 1022 may be optimized to produce specific formulary requirements.

Also, permeable membrane 1008 could potentially be moveable between each pair or plurality of anode electrode 1004 and cathode electrode 1006. Permeable membrane 1008 may be located closer to one electrode than the other electrode to create a larger volume of one species of precursor fluids or solutions. In one aspect, permeable membrane 1008 could be located closer to the anode electrode 1004, thereby creating a greater volume of electrolytic precursor alkaline fluids to be produced. In another aspect, permeable membrane 1008 can be moved closer to one electrode to produce one species of ionized precursor fluid, such as electrolytic acidic fluids, and then later moved closer to the other electrode to produce another species of ionized precursor fluid.

In one embodiment, feedstock brine solution 1022 may be passed through electrolytic cell units 132, 208, which are split electrolytic cells that are operated at a substantially low pressure, such as from about 5 to about 45 pounds per square inch ("psi"). In another aspect, the operating pressure within electrolytic cell units 132, 208, may be from about 12 to about 25 psi.

The present electrolytic chlorine dioxide biocide generation system 100 and portable electrolytic chlorine dioxide biocide generation system 200 may also include other configurations of an ionization apparatus that could include systems using simple electrolysis with or without a membrane (e.g., ported systems or other configuration), variations in plate materials/configurations or any other embodiment that is able to produce an ionized fluid adequate to generate beneficial results during the decontamination process.

In one aspect, electrolytic cell units 132, 208 may be powered by direct current ("DC") power supply produced by converting alternating current ("AC") power supply to DC with transformers, rectifiers, capacitors, regulators, etc. for example. For example, a 120 voltage alternating current ("VAC") supply may be connected with a transformer that converts the power supply to voltage direct current ("VDC"), which may be adjusted or modulated to provide the desired voltage output at power source 1014 for providing the desired voltage and current through electrical leads 1010 and 1012. In another aspect, electrolytic cell units 132, 208 may be powered by a portable or non-portable DC power supply. For example, portable electrolytic chlorine dioxide biocide generation system 200 may include a battery and/or battery pack that is or provides power source 1014 with the desired voltage and current to electrical leads 1010 and 1012. In one embodiment, integral control and monitoring of the current density at electrolytic cell units 132, 208 may be accomplished via solid state engagement and modulation of the electrical supply powering electrolytic cell units 132, 208, such as power source 1014. This may prevent arcing electrical leads 1010 and 1012 while providing control over the electrical supply, resulting in enhanced safety and more consistent formula generation. In one embodiment, power source 1014 provides a VDC of from about 8 to about 14 VDC.

In addition, control units 102, 202 of electrolytic chlorine dioxide biocide generation system 100 and portable electrolytic chlorine dioxide biocide generation system 200 may provide continuous and automated control and monitoring of composition component proportions inputted and outputted from electrolytic cell units 132, 208, including gas and liquid phases, in order to optimize and standardize the properties of the generated electrolytic chlorine dioxide biocides.

Further, control units 102, 202 of electrolytic chlorine dioxide biocide generation system 100 and portable electrolytic chlorine dioxide biocide generation system 200 may provide the continuous and automatic control of reaction resonance times and of the mixing of the formula components through electrolytic cell units 132, 208, and in a certain embodiment via engineered turbulence flow paths extended over calculated lengths within electrolytic cell units 132, 208. By controlling the steps described above in this way, the properties of the generated electrolytic chlorine dioxide biocides are both optimized and consistent.

Moreover, control units 102, 202 of electrolytic chlorine dioxide biocide generation system 100 and portable electrolytic chlorine dioxide biocide generation system 200 may provide enhanced ability for monitoring of key system, sub-system, or unit processes to ensure continuous, top quality compositions of electrolytic chlorine dioxide biocides are achieved. In a certain embodiment, this will allow for remote monitoring of processes and self-diagnostics to maximize electrolytic efficiencies and minimize production interruptions.

The present electrolytic chlorine dioxide biocide generation system further provides for methods of making electrolytic chlorine dioxide biocide compositions.

Figure 11:
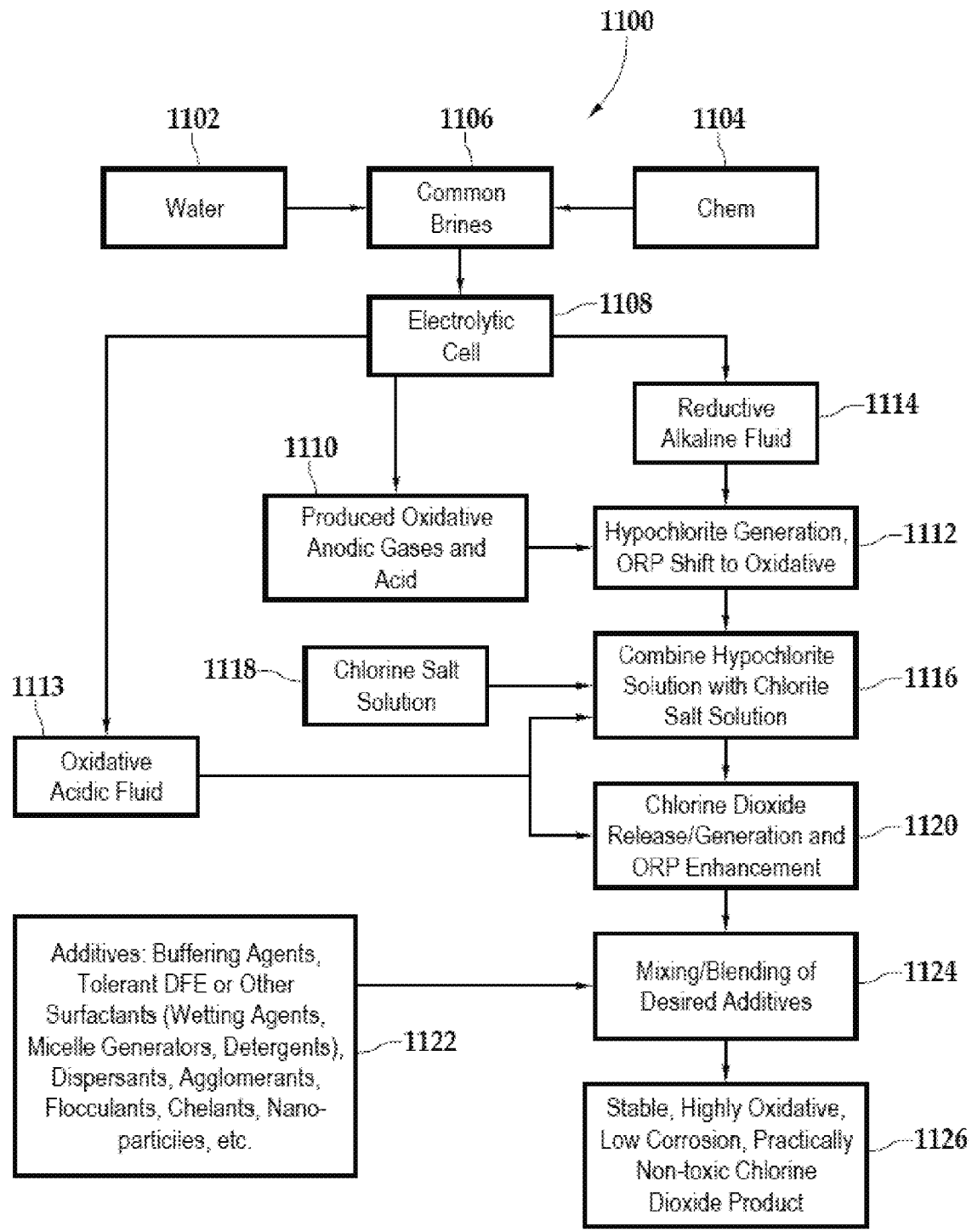
FIG. 11 illustrates a flow sheet of an electrolytic chlorine dioxide biocide generation system according to an embodiment of the present invention.
Figure 12:
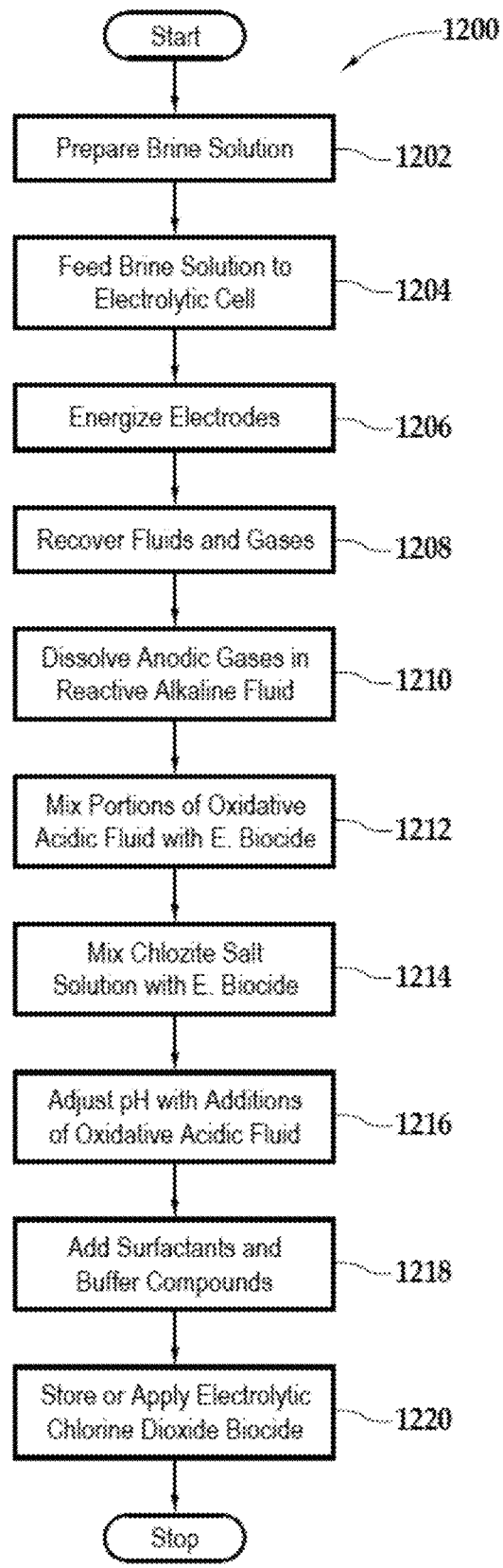
FIG. 12 illustrates a flow diagram of an exemplary process for generating electrolytic chlorine dioxide biocides according to an embodiment of the present invention.

With reference now to FIGS. 11 and 12, a method for making electrolytic chlorine dioxide biocides is schematically illustrated and generally designated 1100 and 1200, respectively. In step 1202, a brine solution is produced by mixing feedstock chemicals from a chemical source 1104, 112, 206 with water provided from a water source 1102, 104, 204. This step may include loading an amount of water into water source 1102, 104, 204 or connecting water source 1102, 104, 204 to a source of water, such as a public utility, lake, vessel, and the like. Additionally, this step may include loading the desired chemical salt into source 1104, 112, 206. The two sources are mixed together to produce a basic brine solution 1106 that may be loaded or inputted into feedstock unit 122, for example.

In step 1204, basic brine solution 1106 is fed into electrolytic cell units 132, 208 as feedstock brine solution 1022.

Water 1024 is also provided to passageway 1018. Electrolytic cell units 132, 208 are used to generate oxidative acidic fluid 1026 and reductive alkaline fluid 1028 from a split cell using, but not limited to, a traditional sodium/potassium chloride salt in an aqueous solution, for example. In step 1206, anode electrode 1004 and cathode electrode 1006 of electrolytic cell units 132, 208, 1108 are energized by supplying electrical power from power source 1014 to electrical leads 1010 and 1012.

In this step, electrolytic cell units 132, 208 may be optimally slow-started via low pulse-width modulation ("PWM") duty cycle and ramped up to allow electrical flow-inhibiting gas bubbles evolved from the electrolyte at the surfaces of anode electrode 1004 and cathode electrode 1006 to form and reach their steady-state level. This prevents startup conditions in which the power requirements are momentarily significantly higher than during all other operating conditions. Net potential/voltage at anode electrode 1004 and cathode electrode 1006 may be maintained as a constant through dynamic control of PWM duty cycle. A solid-state array of transistorized relays configured as an H-Bridge can be utilized to modulate power and polarity for periodic de-scaling and cleaning of electrolytic cell units 132, 208 components.

In step 1208, the generated oxidative acidic fluid 1026, 1113 and reductive alkaline fluid 1028, 1114, anodic gases 1030, 1110, and hydrogen gas 1032 are recovered from electrolytic cell units 132, 208, 1110. The generated oxidative acidic fluid 1026 may have a pH between 0 and 6 and an oxidative (electron deficient or +mV) potential.

In step 1210, the anodic gases 1030, 1110 (chlorine, oxygen, ozone, etc.) that are generated from the anode passageway 1020 may be collected and combined with specified portions of reductive alkaline fluid 1028, 1116 generated in passageway 1018, which may have a pH between 8 and 14, and a reductive (electron rich or −mV) potential, resulting in a simple hypochlorite (bleach) solution with an alkaline pH and normally an oxidative (+mV) potential.

Reductive alkaline fluid 1028 generated in passageway 1018 of electrolytic cell units 132, 208 are generally common hydroxides (e.g. NaOH, KOH). Oxidative acidic fluid 1026 generated in passageway 1020 of electrolytic cell units 132, 208 are generally hydrochloric/hypochlorous acids (HCl, HOCl). Anodic gases 1030 generated in passageway 1020 of electrolytic cell units 132, 208 are generally chlorine, oxygen, ozone, etc. Hydrogen gas 1032 is generally generated in passageway 1018 of electrolytic cell units 132, 208.

In step 1212, anodic gases anodic gases 1030, 1110 may be dissolved or bubbled through (or similar process) a portion of reductive alkaline fluid 1028 to capture the chlorine liberated as a gas from passageway 1020, to form common hypochlorite bleach. As the additional gases from passageway 1020 (e.g. oxygen, ozone, etc.) are dissolved or bubbled through reductive alkaline fluid 1028, they act to help shift the ORP of the electrolytic hypochlorite bleach fluid 1112 from reductive to more oxidative.

In step 1212, portions of the oxidative acidic fluid 1026, 1113 are also blended into the bleach solution to bring the pH down to between 8-9, and the acid further shifts the ORP of the hypochlorite fluid to more oxidative.

In step 1214, the generated acidified hypochlorite bleach fluid solution 1112, 1210 and 1212 is then mixed with an appropriate amount of chlorite salt solution 1118 (e.g. sodium chlorite, potassium chlorite, etc.) at specified rates in order to create a chlorite salt/hypochlorite solution 1214.

The resulting chlorite salt/hypochlorite solution 1214 is mixed with a measured amount of oxidative acidic fluid 1026, 1113 to release a chosen concentration of stable chlorine dioxide at an acidic pH (typically between 0 and 6) 1216. The amount of chlorite salt solution 1118 used is dependent on the final concentration of chlorine dioxide desired. Testing as noted in Table A was conducted at approximately 200 ppm chlorine dioxide, and final concentrations of less than 1000 ppm chlorine dioxide are most common.

In step 1216, portions of oxidative acidic fluid 1026, 1114 (>+1100 mV) are added to the mixed hypochlorite/chlorite salt solution 1028, 1120, 1214 to bring the pH from about 8 to in the range of 2 to 5. Preferably, the pH is adjusted in this step to approximately 3. This step releases the chlorine dioxide from the chlorite solution. The released chlorine dioxide solution should have an ORP value well in excess of +800 mV. At this point the chlorine dioxide solution is still corrosive, but is already more stable than most legacy chlorine dioxide formulations.

In step 1218, additives 1122 are then mixed or blended into the electrolytic chlorine dioxide biocides solution 1124, first to buffer the fluid to near neutral to a pH of from about 5 to a about 8. A wide range of buffers may be used at this step, and potassium/sodium carbonate or similar compounds are preferred in this specific embodiment. Once buffered, pH sensitive surfactants may be added to the electrolytic chlorine dioxide biocide composition. These include oxidative solution tolerant surfactants that do not destroy the solution's ORP or cause any other adverse reactions. Surfactant additives may include alcohol ethoxylates, alykl sulfates and lauroyl sarcosinates, among numerous others. In this example embodiment, surfactants are typically used in the 0.05 to 2.0% range, and are often combined to attain the desired results. The alcohol ethoxylates such as Stepan's Bio-Soft series are used to enhance wetting properties, while alkyl sulfates such as the Stepanol ME-Dry series are included if micelle generation or enhanced cleaning properties are desired. If corrosion is a major concern, Croda's LS-30 surfactant can be added to the formulation to act as a corrosion inhibitor (with or without other surfactant combinations). This description is provided as an example only, and other DFE and traditional surfactants may be used to create a electrolytic chlorine dioxide biocide compositions or formulas with the desired properties.

In one embodiment, a common surfactant load combination is 0.2% of Stepan's Bio-Soft series to enhance wetting combined with 0.2% alykl sulfates such as Stepanol ME-Dry for micelle generation is preferred. This combination was used to generate some of the data in Table A. This electrolytic chlorine dioxide biocide composition retains an ORP in excess of +800 mv during testing, including 60 day shelf life trials.

Numerous other additives including dispersants, agglomerants, flocculants, chelants and nano-particles may also be included in the solution to customize the formulary for specific applications.

In step 1220, the electrolytic chlorine dioxide biocides 1126 may be stored or containerized as desired. In addition, electrolytic chlorine dioxide biocides may be directly applied to surfaces of objects using applicators and the like.

In yet another embodiment, the present electrolytic chlorine dioxide biocide generation system provides for another method of making electrolytic chlorine dioxide biocide compositions.

Figure 13:
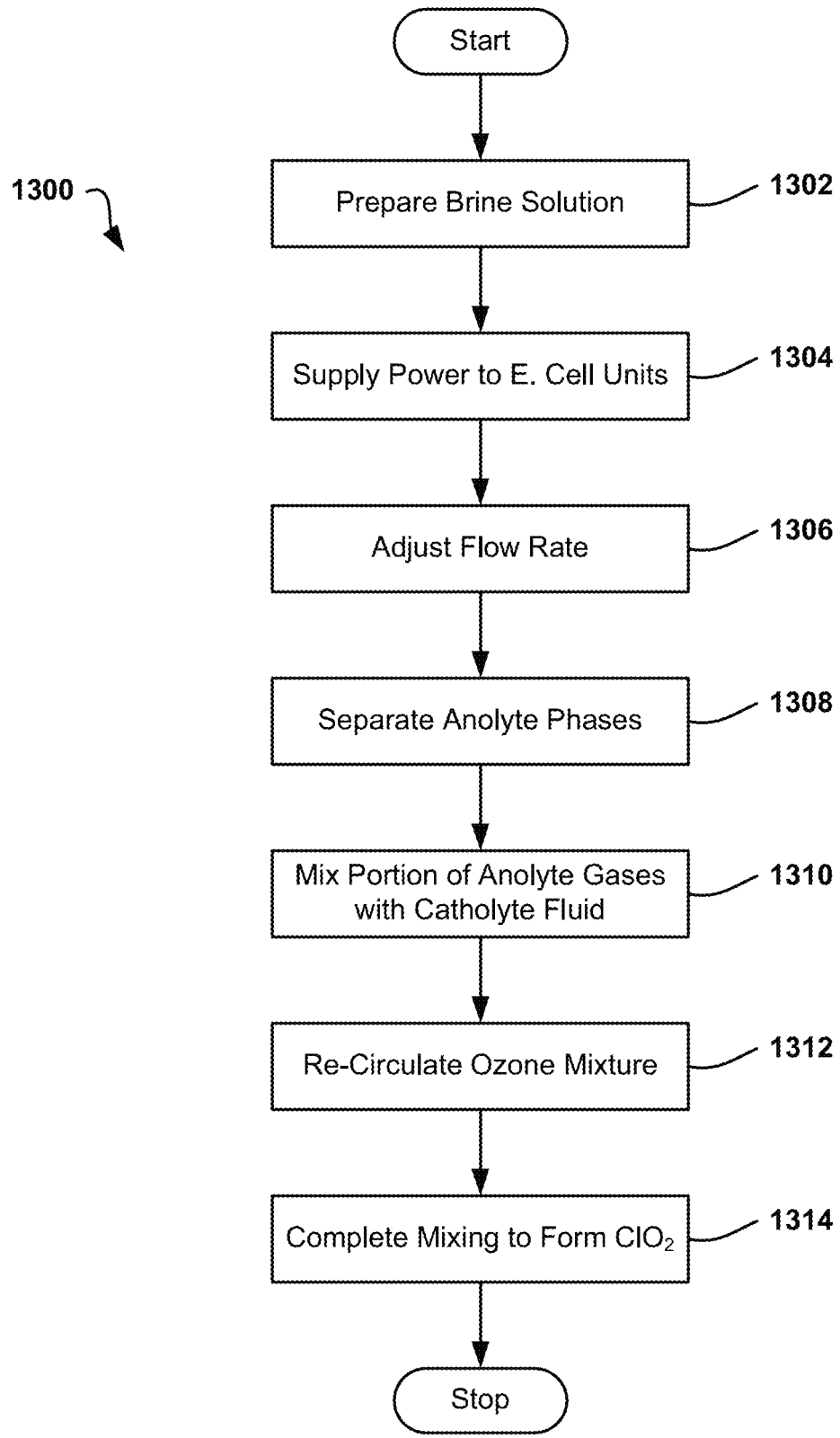
FIG. 13 illustrates a flow diagram of an exemplary batch process for generating electrolytic chlorine dioxide biocides according to another embodiment of the present invention.

With reference now to FIG. 13, another method for making electrolytic chlorine dioxide biocides is schematically illustrated and generally designated 1300. In step 1302, a brine solution is produced by mixing feedstock chemicals from a chemical source 1104, 112, 206 with water provided from a water source 1102, 104, 204. This step may include loading an amount of water into water source 1102, 104, 204 or connecting water source 1102, 104, 204 to a source of water, such as a public utility, lake, vessel, and the like. This step may also include using an ion exchange water softener to remove unwanted constituents from the incoming water source and providing the NaCl brine stock. The brine stock may be metered into the softener output to produce an electrolyte supply stream to the electrolytic cells/banks/reactors. The control of the brine stock metering device output volume may be regulated by a controller that receives an input from a conductivity sensor that is measuring the resulting brine concentration. The resulting input/output control loop may ensure consistent electrolyte concentration. In addition, a second input/output control loop may be utilized with a pressure transducer and variable valve to ensure that the electrolyte is supplied to the reactors at a consistent pressure. Additionally, this step may include loading the desired chemical salt into water source 1104, 112, 206. The two sources are mixed together to produce a basic brine solution 1106 that may be loaded or inputted into feedstock unit 122, for example.

In step 1304, electrical power is supplied to the electrolytic cells/banks/reactors, such as electrolytic cell units 132, by independent and isolated DC voltage power supplies and battery banks, in one example. This step may include that the power be switched and structured by H-bridge configured quadruplet solid state relays. The relays may be controlled by a programmable logic controller ("PLC"), such as part of control unit 102, to deliver reactor power in varying polarity and PWM based on operational mode and corresponding formula variants. Current, voltage, and frequency may be sensed and reported back to the PLC for automatic control and display to the operator interface.

In step 1306, once the electrolyte reaches the electrolytic cells/banks/reactors, flow control valves, which may be located within the electrolytic cells/banks/reactors may manually be adjusted until the desired flow rate is achieved that corresponds to a resonance time for each unit of electrolyte in the electrolytic cells/banks/reactors, such as electrolytic cell units 132. The reaction products are divided into anolyte and catholyte streams inside electrolytic cell units 132. Each bank of electrolytic cell units 132, may have two outlet plumbing connections supplying respective fluid gas mixtures of anolyte interspersed with anolyte gases and catholyte interspersed with catholyte gases, as described herein.

In step 1308, the gases and fluids exit the reactor banks of electrolytic cell units 132, and the anolyte streams are combined in a vessel where buoyant anolyte gases rise and accumulate above the anolyte fluid.

In step 1310, anolyte fluids are then discharged into holding tanks for subsequent processing. This step may include feeding the anolyte gases into an intermediate catholyte (reductive alkaline fluid) holding vessel where a porous nozzle, in one example, maximizes the gas-fluid interface by separating the anolyte gas into a large volume of small bubbles. As the bubbles rise through the catholyte fluid, the gas (chlorine) is consumed in chemical reaction with the catholyte fluid.

In step 1312, the converted anolyte gases form an ozone mixture that may be re-circulated with a gas pump back through the base of the vessel to promote complete conversion of anolyte gases and efficient chemical reactions. The catholyte fluid and anolyte gas reaction forms the precursor sodium hypochlorite bleach mixture reserved for subsequent processing. If the fixed volume of the catholyte reaction vessel is filled in process, the catholyte stream may be diverted to effluent capture for waste processing.

In step 1314, the mixing of the generated hypochlorite solution with the oxidative acidic fluid, the addition of the chlorite salt to the acidified hypochlorite solution, and the mixing of the resulting chlorite salt/hypochlorite solution into the oxidative acidic fluid (HCl/HOCl) to release the $ClO_2$ may all be performed automatically and/or manually, such as by laboratory technicians and the like.

As with any of the processes and steps above, the sensors, pumps, valves, motors, etc. may be controlled by control units 102, 202 of electrolytic chlorine dioxide biocide generation system 100 and portable electrolytic chlorine dioxide biocide generation system 200. This may include the additional steps of separation, isolation, and variable rate metering of any of the generated or produced component gases and liquids into subsequent process steps. This method allows for the accurate measurement of gas and liquid volumes and flow rates and maintains consistent component contributions to the staged reactions used in the generation of the electrolytic chlorine dioxide biocides' compositions, resulting in more consistent formulary generation through time.

The chlorine dioxide generation is unique, as the chlorite salt is not passed through the electrolytic cell, while gaining and maintaining the oxidative benefits of the electrolytic process through the process. This allows for the retention of advantageous electrolytic properties, such as the oxidative potential, while improving chemical conversion efficiency and minimizing waste generation by not requiring a recirculation loop that typically discards unspent chlorite salts as a waste product. The formulation utilizes EPA designated Designed for Environment (DFE) surfactants, as well as others, for wetting properties, micelle generation and corrosion inhibition, while maintaining a near neutral pH. The combination of surfactants and buffering agents is used to decrease the corrosiveness problems common in past chlorine dioxide formulations. Another novel aspect of the chemical processes is that waste products and gases from the electrolytic cell are captured and blended back into the formulation to provide additional formulation stability. This process generates an extremely efficacious biocide that has rapid pathogen kill times, very low toxicity, low corrosivity, dramatically reduced waste generation, and is completely and rapidly biodegradable.

The synergistic use of a chlorine dioxide biocide combined with a carrier fluid that is electrochemically altered to a highly oxidizing potential results in a novel, rapid-acting and highly effective electrolytic chlorine dioxide biocide. The disruption of cellular processes relying on the transfer of electrons is then synergistically assisted by the chlorine dioxide solution by the inhibition of RNA replication and increased cell membrane permeability for high log factor EPA demonstrated efficacy for a 10 minute kill test, using standard EPA test protocols. Thus, by combining two highly effective substances, a carrier fluid highly deficient in electrons and an oxidizer, chlorine dioxide, a biocide is created that directly attacks the cell membrane of microbes, for example, causing rapid microbial death.

An ideal biocide has certain attributes as hypothetically specified by the US Centers for Disease Control (CDC). These ideal attributes are: (1) broad spectrum: should have a wide antimicrobial spectrum; (2) fast acting: should produce a rapid kill; (3) not affected by environmental factors:

should be active in the presence of organic matter (e.g., blood, sputum, feces) and compatible with soaps, detergents, and other chemicals encountered in use; (4) nontoxic: should not be harmful to the user or patient; (5) surface compatibility: should not corrode instruments and metallic surfaces and should not cause the deterioration of cloth, rubber, plastics, and other materials; (6) residual effect on treated surfaces: should leave an antimicrobial film on the treated surface; (7) easy to use with clear label directions; (8) odorless: should have a pleasant odor or no odor to facilitate its routine use; (9) economical: should not be prohibitively high in cost; (10) solubility: should be soluble in water; (11) stability: should be stable in concentrate and use-dilution; (12) cleaner: should have good cleaning properties; and (13) environmentally friendly: should not damage the environment on disposal.

When viewed in the context of this CDC description of the "ideal" disinfectant material, the present electrolytic chlorine dioxide biocides, generated using the description herein, satisfies each of the thirteen stated criteria as specified by the US CDC, and represents a major advancement in the state-of-the-art for biocide generation for efficient biological decontamination and disinfection of hospitals and other health care environments, among many other disinfectant applications.

Other applications for the present electrolytic chlorine dioxide biocides compositions outside of human health care include, but are not limited to; animal facilities, dairies, animal slaughter and meat processing operations; plant growing, processing, and fermentation operations, harvesting, storage, shipping and processing equipment; fixed facility decontamination applications; mineral processing facilities, including bio-processing through enhanced conditions; oil and gas production, transportation, refining, and distribution operations; cooling towers and disinfection of heating and air condition conduits; industrial operations, among many others.

The resulting electrolytic chlorine dioxide biocides have three disinfection mechanisms. The first mechanism, chlorine dioxide reacts readily with amino acids, cysteine, tryptophan, and tyrosine but not with viral RNA. Additional reactions occur with poliovirus RNA, impairing RNA replication and synthesis, free fatty acids, and alteration of the viral capsid proteins.

An additional mechanism is the effect chlorine dioxide has on physiological functions with several studies showing disruption of outer membrane proteins and lipids, which were altered by chlorine dioxide by increased cell membrane permeability.

A third mechanism unique to the electrolytic chlorine dioxide biocides is a carrier fluid with highly oxidizing ORP. It is known that the metabolism of microorganisms and their ability to survive and propagate are influenced by the ORP of the media in which they live. The microorganism lives by biochemical processes involving the intercellular transfer of electrons, which are rapidly removed by the application of the biocide highly deficient in electrons, resulting in extremely rapid and efficacious disruption of cellular processes. Test results demonstrating 5.4 $\log_{10}$ pathogen kills on both gram positive and gram negative microbes in 30 seconds or less at +/−200 ppm ClO2 concentration are provided (See Table A). The electrolytic chlorine dioxide biocides generated by the electrolytic chlorine dioxide biocide generation system has an oxidizing ORP ranging from a few millivolts to over +1,150 millivolts. The oxidizing carrier fluid helps in stripping electrons from microorganisms' cellular processes, thus assisting in weakening and killing the microbes by cell destabilization and by destroying the integrity of the cell membrane.

The described process is designed to produce electrolytic chlorine dioxide biocides with stability in excess of greater than days with enhanced Oxidative-Reductive Potential (ORP), and often using EPA designated Designed for Environment (DFE) additives. The resulting electrolytic chlorine dioxide biocides solutions have undergone extensive third party testing for microbial efficacy and toxicology determination. This data is presented in Table A below. This independent, third party testing using EPA protocols, clearly demonstrates a product meeting the CDC criteria, namely: (1) broad spectrum has been demonstrated against a wide range of gram positive and gram negative organisms, (2) fast acting documented by 30 second kill rates at 5.4 $\log_{10}$, (3) not affected by environmental factors as documented by the 5% organic challenge, (4) nontoxic with an EPA Class IV toxicity (Practically Non-Toxic), (5) surface compatibility, showing corrosion levels less than even non-chlorinated tap water, (6) residual effect on treated surfaces, shown by lab testing, (7) easy to use applied as an aqueous solution with standard or specialized equipment, (8) odorless with a slight, short-lived chloro-odor, (9) economical process and chemical costs are nominal, (10) solubility ClO2 is soluble in water, (11) stability as documented with 60 day EPA efficacy tests, (12) cleaner the addition of specific additives enhances the surface active properties of the carrier fluid for improved cleaning (13) environmentally friendly, designed to rapidly break down in the environment.

The efficacy of the formulation is demonstrated in the independent laboratory analysis using standard Good Laboratory Practices (GLP) protocols provided in Table B. This data set shows the efficacy, stability and category IV toxicity (the lowest level of toxicity per US EPA, described as "practically non-toxic) of the electrolytic chlorine dioxide biocide formulations. These data sets were compiled and provided for US EPA registration, under EPA test protocols, which has been granted; U.S. EPA Registration Number 87492-1 on 4 Oct. 2010.

In one aspect, the electrolytic chlorine dioxide biocides are effective in killing biological contamination, which can be biologic matter present, located on or near a substrate surface, and which can be removed and spread by contact, air movement or other mechanical or physical means, for example.

The electrolytic chlorine dioxide biocides uses two highly effective substances, a carrier fluid, highly deficient in electrons and an oxidizer, such as, but not limited to chlorine dioxide. The present electrolytic chlorine dioxide biocides directly attacks the cell membrane of a microbe, for example, causing rapid death with >5.4 $\text{Log}_{10}$ reduction in 30 seconds. The electrolytic chlorine dioxide biocides have a deliberate and engineered electric potential in the carrier fluid as a specific pathogen killing mechanism. Also, the present ClO2 formulations have been shown to be highly effective against biofilms and biofilm-forming microbes. The formulations' effectiveness against biofilms can be enhanced by the addition of specific surfactants.

Additionally, the electrolytic chlorine dioxide biocides have high stability that is gained through the novel chemical process using electrolytic cell units 132, 208 to generate aqueous electrolytic chlorine dioxide biocide solutions that do not pass the chlorite salt solution through the electrolytic cell. It further utilizes certain waste products from electrolytic cell units 132, 208 to enhance and stabilize the aqueous electrolytic chlorine dioxide biocides for extended periods of time.

The present electrolytic chlorine dioxide biocides have third party test results attesting to broad spectrum pathogen killing ability, including, but not limited to: *Pseudomonas aeruginosa*, Staph (*Staphylococcus aureus*), MRSA (Methicillin Resistant *Staphylococcus aureus*), VRE (Vancomycin Resistant *Enterococcus faecalis*), H1N1 (Influenza Type A), HIV Type 1, Hepatitis, *Rhinovirus, Salmonella enteric, C diff* (*Clostridium difficile*), *Acinetobacter baumannii, Klebsiellia pneumonia, Vancomycin Resistant Staphylococcus aureus*, and *Campylobacter jejuni*, among others. These results are provided below.

Example 1

A composition produced by the electrolytic chlorine dioxide biocide generation system was tested against microbes and the results are shown below in Table 1. The results were achieved by an independent laboratory, ATS Laboratories, Eagan, Minn., per U.S. EPA 40 CFR Part 158 Protocol—AOAC Germicidal Spray Method.

TABLE 1

| Microorganism | 10 Minute Kill Level - % | Organic Load - % | EPA Demonstrated Efficacy - 10 Minute Kill |
|---|---|---|---|
| *Pseudomonas aeruginosa* | | | |
| Lot 1 | 100% | Not Required by EPA | Yes |
| Lot 2 | 100% (59/60 cultures) | Not Required by EPA | Yes |
| Lot 3 | 100% | Not Required by EPA | Yes |
| *Staph* (*Staphylococcus aureus*) | | | |
| Lot 1 | 100% | Not Required by EPA | Yes |
| Lot 2 | 100% | Not Required by EPA | Yes |
| Lot 3 | 100% | Not Required by EPA | Yes |
| MRSA (Methicillin Resistant *Staphylococcus aureus*) | | | |
| Lot 1 | 100% | Not Required by EPA | Yes |
| Lot 2 | 100% | Not Required by EPA | Yes |
| VRE (Vancomycin Resistant *Enterococcus faecalis*) | | | |
| Lot 1 | 100% | Not Required by EPA | Yes |
| Lot 2 | 100% | Not Required by EPA | Yes |
| H1N1 (Influenza Type A) | | | |
| Lot 1 | 100% | 1% | Yes |
| Lot 2 | 100% | 1% | Yes |
| HIV Type 1 | | | |
| Lot 1 | 100% | 5% | Yes |
| Lot 2 | 100% | 5% | Yes |
| Hepatitis | | | |
| Lot 1 | 100% | 1% | Yes |
| Lot 2 | 100% | 1% | Yes |
| Rhinovirus | | | |
| Lot 1 | 100% | 1% | Yes |
| Lot 2 | 100% | 1% | Yes |
| *Salmonella enteric* | | | |
| Lot 1 | 100% | Not Required by EPA | Yes |
| Lot 2 | 100% | Not Required by EPA | Yes |
| Lot 3 | 100% | Not Required by EPA | Yes |
| *C diff* (*Clostridium difficile*)₂ | | | |
| Lot 1 | 99.5% | Not Required by EPA | No* |
| Lot 2 | 92.8% | Not Required by EPA | No* |
| Lot 3 | 99.8% | Not Required by EPA | No* |
| *C diff* (*Clostridium difficile*)₂ | | | |
| Spray test results - 10 minute exposure | 5.7 log reduction | Not Required by EPA | No* |
| Spray test results - 30 minute exposure | 6.1 log reduction (complete inactivation) | Not Required by EPA | No* |
| *Acinetobacter baumannii* | | | |
| Lot 1 | 100% | Not Required by EPA | Yes |
| Lot 2 | 100% | Not Required by EPA | Yes |
| *Klebsiellia pneumonia* | | | |
| Lot 1 | 100% | Not Required by EPA | Yes |
| Lot 2 | 100% | Not Required by EPA | Yes |
| Vancomycin Resistant *Staphylococcus aureus* | | | |
| Lot 1 | 100% | 5% | Yes |
| Lot 2 | 100% | 5% | Yes |
| *Campylobacter jejuni* | | | |
| Lot 1 | 100% | 5% | Yes |
| Lot 2 | 100% | 5% | Yes |

The composition was then subjected to a long-term (60 day) shelf life product study. The Long-Term (60 day) Shelf Life Product Study were performed by ATS Laboratories, Eagan, Minn. (test samples generated 60 days prior to testing to confirm Electro-Biocide's unique long term shelf life stability)

Test Substance: Electro Biocide Lot—Long Term Shelf Life Test, Dec. 7, 2009
Test Organisms: *Pseudomonas aeruginosa, Staphylococcus aureus, Salmonella enterica*
Exposure Time: 10 minutes
Exposure Temperature: room temperature (21° C.)
# of Carriers Tested: 60 per batch
Organic Soil Load Used in Testing?: No
Control Results: Carrier Quantitation Control:
*Pseudomonas Aeruginosa:* $7.7 \times 10^6$ CFU/carrier
*Staphylococcus Aureus:* $1.51 \times 10^6$ CFU/carrier
*Salmonella Enterica:* $3.1 \times 10^4$ CFU/carrier
Test Results:
Electro Biocide Lot Long Term Shelf Life Test Dec. 7, 2009 tested against *Pseudomonas aeruginosa:*
0 out of 60 carriers were positive for the test organism (PASS)

Electro Biocide Lot Long Term Shelf Life Test Dec. 7, 2009 tested against *Staphylococcus aureus:*
    0 out of 60 carriers were positive for the test organism (PASS)

Electro Biocide Lot Long Term Shelf Life Test Dec. 7, 2009 tested against *Salmonella enterica:*
    0 out of 60 carriers were positive for the test organism (PASS)

As seen in the test summary above, the electrolytic chlorine dioxide biocides were extremely effective at killing the target organisms 60 days after generation of the formulation. While the concept of the described technology is to create and customize disinfectant formulas as needed and at or just prior to the time of use, these extended shelf-life properties enhance the utility, usability and storability of the unique ClO2 solutions. This revolutionary capability means users can customize, generate and effectively store quantities of the formulations in anticipation of imminent decontamination operations. The capability to do so significantly improves the logistical challenges associated with typical Cl02 generators. With this unique technology, it is now possible to centralize formulation generators, create needed volumes of product and then transport the solutions to the decontamination site.

After proving efficacy in the EPA-mandated 10 minute tests, additional testing was undertaken to determine the effectiveness of the unique electrolytic chlorine dioxide biocides. Two gram positive (MRSA, VRE) and two gram negative (*Pseudomonas aeruginosa, Acinetobacter baumanii*) microbes were chosen for efficacy testing at 30, 60, 90, 120 and 150 seconds of contact with the electrolytic chlorine dioxide biocides. The following provides results from those tests, performed at ATS Labs in Eagan, Minn.

Protocol #: ADN010911210.TK
    Test Substance: Electro-BioCide (Lot #1001010-1)
    Test Organisms: Methicillin Resistant *Staphylococcus aureus*—MRSA (ATCC 33592), *Acinetobacter baumannii* (ATCC 191206), Vancomycin Resistant *Entercoccus faecalis*—VRE (ATCC 51575), & *Pseudomonas aeruginosa* (ATCC 15442)
    Exposure times: 30, 60, 90, 120, & 150 seconds
    Exposure temperature: Ambient (21° C.)
    Control Results
    Test Population Control Results
    Methicillin Resistant *Staphylococcus aureus*—MRSA: $1.33 \times 10^6$ ($6.124 \, Log_{10}$) CFU/mL
    *Acinetobacter baumannii:* $8.5 \times 10^5$ ($5.93 \, Log_{10}$) CFU/mL
    Vancomycin Resistant *Entercoccus faecalis*—VRE: $1.03 \times 10^6$ ($6.013 \, Log_{10}$) CFU/mL
    *Pseudomonas aeruginosa:* $1.41 \times 10^6$ ($6.149 \, Log_{10}$) CFU/mL
    Test results (Lot #1001010-1)
    Methicillin Resistant *Staphylococcus aureus*—MRSA 30 seconds: <5 ($0.7 \, Log_{10}$) surviving CFU/mL→99.999% (>$5.4 \, Log_n$) reduction
60 seconds: <5 ($0.7 \, Log_{10}$) surviving CFU/mL→99.999% (>$5.4 \, Log_n$) reduction
90 seconds: <5 ($0.7 \, Log_{10}$) surviving CFU/mL→99.999% (>$5.4 \, Log_n$) reduction
120 seconds: <5 ($0.7 \, Log_{10}$) surviving CFU/mL→99.999% (>$5.4 \, Log_n$) reduction
150 seconds: <5 ($0.7 \, Log_{10}$) surviving CFU/mL→99.999% (>$5.4 \, Log_n$) reduction

*Acinetobacter baumannii*

30 seconds: <5 ($0.7 \, Log_{10}$) surviving CFU/mL→99.999% (>$5.2 \, Log_n$) reduction
60 seconds: <5 ($0.7 \, Log_{10}$) surviving CFU/mL→99.999% (>$5.2 \, Log_n$) reduction
90 seconds: <5 ($0.7 \, Log_{10}$) surviving CFU/mL→99.999% (>$5.2 \, Log_n$) reduction
120 seconds: <5 ($0.7 \, Log_{10}$) surviving CFU/mL→99.999% (>$5.2 \, Log_n$) reduction
150 seconds: <5 ($0.7 \, Log_{10}$) surviving CFU/mL→99.999% (>$5.2 \, Log_n$) reduction Vancomycin Resistant *Entercoccus faecalis*—VRE 30 seconds: <5 ($0.7 \, Log_{10}$) surviving CFU/mL→99.999% (>$5.3 \, Log_n$) reduction
60 seconds: <5 ($0.7 \, Log_{10}$) surviving CFU/mL→99.999% (>$5.3 \, Log_n$) reduction
90 seconds: <5 ($0.7 \, Log_{10}$) surviving CFU/mL→99.999% (>$5.3 \, Log_n$) reduction
120 seconds: <5 ($0.7 \, Log_{10}$) surviving CFU/mL→99.999% (>$5.3 \, Log_n$) reduction
150 seconds: <5 ($0.7 \, Log_{10}$) surviving CFU/mL→99.999% (>$5.3 \, Log_n$) reduction

*Pseudomonas aeruginosa*

30 seconds: <5 ($0.7 \, Log_{10}$) surviving CFU/mL→99.999% (>$5.4 \, Log_n$) reduction
60 seconds: <5 ($0.7 \, Log_{10}$) surviving CFU/mL→99.999% (>$5.4 \, Log_n$) reduction
90 seconds: <5 ($0.7 \, Log_{10}$) surviving CFU/mL→99.999% (>$5.4 \, Log_n$) reduction
120 seconds: <5 ($0.7 \, Log_{10}$) surviving CFU/mL→99.999% (>$5.4 \, Log_n$) reduction
150 seconds: <5 ($0.7 \, Log_{10}$) surviving CFU/mL→99.999% (>$5.4 \, Log_n$) reduction The statistical test analysis shows complete inactivation of all four organisms after only 30 seconds of contact. These accelerated kill rates are unprecedented for a disinfectant solution containing only a couple of hundred parts per million of active ingredients, and clearly shows the unique characteristics of the formulations herein described.

While the formulation has shown extraordinary effectiveness at low concentrations and as a low corrosion formula, the following test results serve to substantiate the exceptional properties of this technology. The following six-pack of US EPA mandated tests were performed at Tox Monitor Laboratories in Oak Park, Ill., per established EPA protocols. Category IV toxicity is the lowest level of human and animal toxicity achievable per EPA guidelines.

Toxicity Testing—Laboratory Results—Jan. 29, 2010

TABLE B

| TEST | CATEGORY | DEFINITION |
| --- | --- | --- |
| Acute Eye Irritation | IV | Practically Non-Toxic* |
| Acute Dermal Toxicity | IV | Practically Non-Toxic* |
| Acute Inhalation | IV | Practically Non-Toxic* |
| Acute Oral Toxicity | IV | Practically Non-Toxic* |
| Acute Skin Irritation | IV | Practically Non-Toxic* |
| Acute Skin Sensitization | IV | Practically Non-Toxic* |

*Category IV (per EPA Label Review Manual, Chapter 7) instructs "No statements are required".

Overall Category IV rating for Electro-Biocide™.

The electrolytic chlorine dioxide biocide generation system applies environmentally benign buffering materials and additive technologies to the produced formularies in order to minimize the corrosive effects of the oxidizing formulas. The result is that the generated electrolytic chlorine dioxide biocides have been shown to cause very little corrosion on traditional mild steel test coupons, with corrosion after 1-hour of wet contact with subsequent air dry being less for the chlorine dioxide formulary than for even non-chlorinated tap water at a 7 pH.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed:

1. A method for electrolytically generating a biocide having an electron deficient carrier fluid and chlorine dioxide, comprising:
    providing a carrier fluid;
    providing a pair of electrodes interposed by a permeable membrane within a vessel for creating a first passageway and a second passageway, an anode electrode of the pair of electrodes disposed in the first passageway and a cathode electrode of the pair of electrodes disposed in the second passageway;
    flowing the carrier fluid through the vessel;
    applying an electric potential to the pair of electrodes to produce an anolyte fluid, an anolyte gas, a catholyte fluid, and a catholyte gas in the vessel;
    removing the anolyte fluid, the anolyte gas, the catholyte fluid, and the catholyte gas from the vessel;
    mixing a portion of the anolyte gas with the catholyte fluid to produce an ozone gas and hypochlorite bleach mixture;
    re-circulating a portion of the ozone gas with the ozone gas and hypochlorite bleach mixture to further shift the ORP of the hypochlorite solution to more oxidative;
    mixing a portion of the anolyte fluid with the hypochlorite bleach solution to lower the pH and further shift the ORP to more oxidative;
    mixing a chlorite brine with the hypochlorite bleach solution to produce a chlorite brine/hypochlorite bleach solution mixture; and
    mixing a portion of the anolyte fluid with the chlorite brine/hypochlorite bleach solution mixture to the produce the biocide.

2. The method for electrolytically generating a biocide of claim 1 further wherein the providing a carrier fluid comprises:
    flowing a water source through an ion exchange water softener to remove contaminants and to provide sodium chloride to produce the carrier fluid.

3. The method for electrolytically generating a biocide of claim 2 further comprising:
    determining the resonance time through the ion exchange water softener by monitoring the conductivity of the carrier fluid outflow.

4. The method for electrolytically generating a biocide of claim 3 wherein the monitoring further comprises:
    monitoring at least one of pH and ORP of the oxidative acidic fluid and the reductive alkaline fluid.

5. The method for electrolytically generating a biocide of claim 1 further comprising:
    monitoring the pressure of the carrier fluid to the vessel for providing a desired volume of carrier fluid in the vessel.

6. The method for electrolytically generating a biocide of claim 1 wherein the applying an electric potential comprises:
    supplying the electric potential from one or more of a DC voltage power supply and battery banks.

7. The method for electrolytically generating a biocide of claim 1 wherein the applying an electric potential further comprises:
    switching and structuring the electric potential with an H-bridge configured quadruplet solid state relay.

8. The method for electrolytically generating a biocide of claim 7 further comprising:
    controlling the H-bridge configured quadruplet solid state relay with a programmable logic controller for delivering the electric potential in varying polarity and pulse width modulation.

9. The method for electrolytically generating a biocide of claim 1, further comprising:
    flowing the anolyte fluid and anolyte gas from the vessel to a second vessel having sufficient headspace for phase separation of the anolyte gas above the anolyte fluid.

10. The method for electrolytically generating a biocide of claim 1 wherein the mixing a portion of the anolyte gas with the catholyte fluid comprises:
    aerating the catholyte fluid with the anolyte gas in the second vessel.

11. The method for electrolytically generating a biocide of claim 1, further comprising:
    adjusting the mineral content of the brine fluid.

12. The method for electrolytically generating a biocide of claim 1, wherein the method is a batch mix process.

13. The method for electrolytically generating a biocide of claim 1, wherein the method is a continuous flow process.

* * * * *